(12) United States Patent
Sisk et al.

(10) Patent No.: US 7,494,805 B2
(45) Date of Patent: Feb. 24, 2009

(54) EXPRESSION CASSETTE AND VECTOR FOR TRANSIENT OR STABLE EXPRESSION OF EXOGENOUS MOLECULES

(75) Inventors: William P. Sisk, Boxborough, MA (US); Holly Prentice, Carlisle, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 329 days.

(21) Appl. No.: 10/545,420

(22) PCT Filed: Feb. 13, 2004

(86) PCT No.: PCT/US2004/004407

§ 371 (c)(1),
(2), (4) Date: Aug. 12, 2005

(87) PCT Pub. No.: WO2004/074439

PCT Pub. Date: Sep. 2, 2004

(65) Prior Publication Data

US 2006/0141625 A1 Jun. 29, 2006

Related U.S. Application Data

(60) Provisional application No. 60/448,179, filed on Feb. 14, 2003.

(51) Int. Cl.
*C12N 15/63* (2006.01)
(52) U.S. Cl. ............... 435/320.1; 536/24.1; 514/44
(58) Field of Classification Search ................ None
See application file for complete search history.

(56) References Cited

U.S. PATENT DOCUMENTS

| | | | |
|---|---|---|---|
| 5,658,759 A | 8/1997 | Bebbington | |
| 6,194,176 B1 | 2/2001 | Newgard et al. | |
| 6,309,634 B1 * | 10/2001 | Bankiewicz et al. | 424/93.2 |
| 6,423,693 B1 | 7/2002 | Schwartz et al. | |
| 2002/0052480 A1 | 5/2002 | Park et al. | |
| 2002/0065213 A1 | 5/2002 | Debs | |
| 2003/0120060 A1 | 6/2003 | Gonczol et al. | |
| 2003/0235823 A1 | 12/2003 | Caldwell et al. | |

FOREIGN PATENT DOCUMENTS

| | | |
|---|---|---|
| DE | 10133407 A1 | 1/2003 |
| RU | 2148647 | 5/2000 |
| WO | WO 89/01036 A | 2/1989 |
| WO | WO 93/08207 A1 | 4/1993 |
| WO | WO 96/39154 A1 | 12/1996 |
| WO | WO 96/40918 A2 | 12/1996 |
| WO | WO 97/03211 A1 | 1/1997 |
| WO | WO 01/29208 A | 4/2001 |
| WO | WO 01/94599 A1 | 12/2001 |
| WO | WO 02/02765 A2 | 1/2002 |
| WO | WO 2004/074439 A2 | 9/2004 |

OTHER PUBLICATIONS

Brewer, C.B., "Cytomegalovirus Plasmid Vectors for Permanent Lines of Polarized Epithelial Cells," *Methods Cell Biol.* 43:233-245, Academic Press, Inc. (1994).
Stenberg, R.M., et al., "Structural Analysis of the Major Immediate Early Gene of Human Cytomegalovirus," *J. Virol.* 49:190-199, American Society for Microbiology (1984).
Thomsen, D.R., et al., "Promoter-regulatory region of the major immediate early gene of human cytomegalovirus," *Proc. Natl. Acad. Sci.* 81:659-663, The National Academy of Sciences (1984).
Suuplementary European Search Report for European Application No. EP 04 71 1259, European Patent Office, Munich, DE, mailed on Jun. 21, 2006.
Altschul, S.F., et al., Basic Local Alignment Search Tool, *J. Mol. Biol.* 215:403-410, Academic Press Ltd. (1990).
Brasel, K., et al., "Hematologic Effects of flt3 Ligand In Vivo in Mice," *Blood* 88:2004-2012, The American Society of Hematology (1996).
Chaudhary, V.K., et al., "A recombinant immunotoxin consisting of two antibody variable domains fused to *Pseudomonas* exotoxin," *Nature* 339:394-397, Macmillan Magazines Ltd. (1989).
Colbère Garapin, F., et al., "A New Dominant Hybrid Selective Marker for Higher Eukaryotic Cells," *J. Mol. Biol.* 150:1-14, Academic Press Inc. (1981).
Henikoff, S. and Henikoff, J.G., "Amino acid substitution matrices from protein blocks," *Proc. Natl. Acad. Sci. USA* 89:10915-10919, The National Academy of Sciences (1992).
Karlin, S. and Altschul, S.F., "Applications and statistics for multiple high-scoring segments in molecular sequences," *Proc. Natl. Acad. Sci. USA* 90:5873-5877, The National Academy of Sciences (1993).
Kaufman, R.J., "Selection and Coamplification of Heterologous Genes in Mammalian Cells," *Methods Enzymology* 185:537-566, Academic Press, Inc. (1990).
Kaufman, R.J., et al., "Synthesis, Processing, and Secretion of Recombinant Humana Factor VIII Expressed in Mammalian Cells," *J. Biol. Chem.* 263:6352-6362, The American Society for Biochemistry and Molecular Biology, Inc. (1988).
Kozak, M., "Point Mutations Define a Sequence Flanking the AUG Initiator Codon That Modulates Translation by Eukaryotic Ribosomes," *Cell* 44:283-292, Cell Press (1986).
Larrick, J.W., et al., "Polymerase Chain Reaction Using Mixed Primers: Cloning of Human Monoclonal Antibody Variable Region Genes from Single Hybridoma Cells," *Bio/Technology* 7:934-938, Nature Publishing Co. (1989).
Lowy, I., et al., "Isolation of Transforming DNA: Cloning the Hamster aprt Gene," *Cell* 22:817-823, The MIT Press (1980).
MacGregor, G.R. and Caskey, C.T., "Construction of plasmids that express *E. coli* β-galactosidase in mammalian cells," *Nucleic Acids Res.* 17:2365, IRL Press (1989).

(Continued)

*Primary Examiner*—James S Ketter

(74) *Attorney, Agent, or Firm*—Sterne, Kessler, Goldstein & Fox, P.L.L.C.

(57) ABSTRACT

The disclosure provides an expression cassette and a vector comprising the cassette for expression of a polynucleotide. The expression cassette includes a promoter/enhancer, an intervening region, and a polyadenylation signal domain. Expression systems and methods of using the expression cassette and vector are also provided.

44 Claims, 15 Drawing Sheets

OTHER PUBLICATIONS

Mata, J.E., et al., "A Hexameric Phosphorothioate Oligonucleotide Telomerase Inhibitor Arrests Growth of Burkitt's Lymphoma cells in Vitro and in Vivo," *Tox. Appl. Pharm. 144*:189-197, Academic Press (1997).

McKinnon, P., et al., "Expression, purification and characterization of secreted recombinant human insulin-like growth factor-I (IGF-I) and the potent variant des(1-3)IGF-I in Chinese hamster ovary cells," *J. Mol. Endo. 6*:231-239, Journal of Endocrinology Ltd. (1991).

Milligan, J.F., et al., "Current concepts in Antisense Drug Design," *J. Med. Chem. 36*:1923-1937, American Chemical Society (1993).

Mulligan, R.C. and Berg, P., "Selection for animal cells that express the *Escherichia coli* gene coding for xanthine-guanine phosphoribosyltransferase," *Proc. Natl. Acad. Sci. USA 78*:2072-2076, The National Academy of Sciences (1981).

Needleman, S.B. and Wunsch, C.D., "A General Method Applicable to the Search for Similarities in the Amino Acid Sequence of Two Proteins," *J. Mol. Biol. 48*:443-453, Academic Press, Inc. (1970).

O'Hare, K., et al., "Transformation of mouse fibroblasts to methotrexate resistance by a recombinant plasmid expressing a prokaryotic dihydrofolate reductase," *Proc. Natl. Acad. Sci. USA 78*:1527-1531, The National Academy of Sciences (1981).

Pearson, W.R. and Lipman, D.J., "Improved tools for biological sequence comparison," *Proc. Natl. Acad. Sci. USA 85*:2444-2448, The National Academy of Sciences (1988).

Riechmann, L., et al., "Reshaping human antibodies for therapy," *Nature 332*:323-327, Macmillan Magazines Ltd. (1988).

Roberts, S., et al., "Generation of an antibody with enhanced affinity and specificity for its antigen by protein engineering," *Nature 328*:731-734, Macmillan Magazines Ltd. (1987).

Samstag, W., et al., "Synthesis and Properties of New Antisense Oligodeoxynucleotides Containing Benzylphosphonate Linkages," *Antisense Nucleic Acid Drug Development 6*:153-156, Mary Ann Liebert, Inc. (1996).

Santerre, R.F., et al., "Expression of prokaryotic genes for hygromycin B and G418 resistance as dominant-selection markers in mouse L cells," *Gene 30*:147-156, Elsevier Science Publishers (1984).

Shine, J. and Dalgarno, L., "The 3'-Terminal Sequence of *Escherichia coli* 16S Ribosomal RNA: Complementarity to Nonsense Triplets and Ribosome Binding Sites," *Proc. Natl. Acad. Sci. USA 71*:1342-1346, The National Academy of Sciences (1974).

Smith, T.F. and Waterman, M.S., "Comparison of Biosequences," *Adv. Appl. Math. 2*:482-489, Academic Press, Inc. (1981).

Strauss-Soukop, J.K., et al. "Effects of Neutralization Pattern and Stereochemistry on DNA Bending by Methylphosphonate Substitutions," *Biochem. 36*:8692-8698, American Chemical Society (1997).

Szybalska, E.H. and Szybalski, W., "Genetics of Human Cell Lines, IV. DNA-Mediated Heritable Transformation of a Biochemical Trait," *Proc. Natl. Acad. Sci. USA 48*:2026-2034, The National Academy of Sciences (1962).

Tijssen, P., "Hybridization with Nucleic Probes," in *Laboratory Techniques in Biochemistry and Molecular Biology*, van der Vliet, P.C., ed., Elsevier Science Publishers B.V., AE Amsterdam, The Netherlands, Chapter 2, pp. 20-78 (1993).

Urlaub, G. and Chasin, L.A., "Isolation of Chinese hamster cell mutants deficient in dihydrofolate reductase activity," *Proc. Natl. Acad. Sci. USA 77*:4216-4220, The National Academy of Sciences (1980).

Urlaub, G., et al., "Deletion of the Diploid Dihydrofolate Reductase Locus from Cultured Mammalian Cells," *Cell 33*:405-412, The MIT Press (1983).

Varani, G. and Nagi, K., "RNA Recognition by RNP Proteins During RNA Processing," *Annu. Rev. Biophys. Biomol. Struct. 27*:407-445, Annual Reviews (1998).

Verhoeyen, M., et al., "Reshaping Human Antibodies: Grafting an Antilysosome Activity," *Science 239*:1534-1536, American Association for the Advancement of Science (1988).

Wigler, M., et al., "Transfer of Purified Herpes Virus Thymidine Kinase Gene to Cultured Mouse Cells," *Cell 11*:223-232, The MIT Press (1977).

Wigler, M., et al., "Transformation of mammalian cells with an amplifiable dominant-acting gene," *Proc. Natl. Acad. Sci. USA 77*:3567-3570, The National Academy of Sciences (1980).

Wittop Koning, T.H. and Schümperli, D., "RNAs and ribonucleoproteins in recognition and catalysis," *Eur. J. Biochem. 219*:25-42, Springer-Verlag (1994).

Wood, C.R., et al., "High Level Synthesis of Immunoglobulins in Chinese Hamster Ovary Cells," *J. Immunol. 145*:3011-3016, The American Association of Immunologists (1990).

NCBI Entrez, GenBank Report, Accession No. K00470, Seeburg, P.H., Entry Date Sep. 2005.

NBCI Entrez, GenBank Report, Accession No. U47121, Brondyk, W.H. and Groskreutz, D.J., Entry Date Sep. 2005.

NBCI Entrez, GenBank Report, Accession No. U89938, Holtz, A. and Lou, Y., Entry Date Sep. 2005.

Dialog File 351, Accession No. 2003-278290/200327, English language abstract for DE 10133407 A1 (listed as document FP10 on accompanying PTO/SB/08A), (2007).

Esp@cenet English language abstract for RU 2148647 (listed as document FP11 on accompanying PTO/SB/08A), (2007).

Eurasian Search Report for Eurasian Application No. 200700469, Eurasian Patent Office, Moscow, Russia, completed on Jun. 1, 2007.

* cited by examiner

Annotated p V90 sequence

```
   1 AGCTTGACATTGATTATTGACTAGTTATTAATAGTAATCAATTACGGGGTCATTAGTTCATAGCCCATATATGGAGTTCCGCGTTA
  87 CATAACTTACGGTAAATGGCCCGCCTGGCTGACCGCCCAACGACCCCCGCCCATTGACGTCAATAATGACGTATGTTCCCATAGTA
 173 ACGCCAATAGGGACTTTCCATTGACGTCAATGGGTGGAGTATTTACGGTAAACTGCCCACTTGGCAGTACATCAAGTGTATCATAT
 259 GCCAAGTACGCCCCCTATTGACGTCAATGACGGTAAATGGCCCGCCTGGCATTATGCCCAGTACATGACCTTATGGGACTTTCCTA
 345 CTTGGCAGTACATCTACGTATTAGTCATCGCTATTACCATGGTGATGCGGTTTTGGCAGTACATCAATGGGCGTGGATAGCGGTTT
 431 GACTCACGGGGATTTCCAAGTCTCCACCCCATTGACGTCAATGGGAGTTTGTTTTGGCACCAAAATCAACGGGACTTTCCAAAATG
                                                                          TATA box(576)
 517 TCGTAACAACTCCGCCCCATTGACGCAAATGGGCGGTAGGCGTGTACGGTGGGAGGTCTATATAAGCAGAGCTCGTTTAGTGAA
         CAP(603)
 601 CCGTCAGATCGCCTGGAGACGCCATCCACGCTGTTTTGACCTCCATAGAAGACACCGGGACCGATCCAGCCTCCGCGGCCGGGAAC
 687 GGTGCATTGGAACGCGGATTCCCCGTGCCAAGA
         splice donor(719)
 720 GTGACGTAAGTACCGCCTATAGAGTCTATAGGCCCACCCCCTTGGCTTCTTATGGATGCTATACTGTTTTTGGCTTCCCGTCTATA
 806 CACCCCCGCTTCCTCATGTTATAGGTGATGGTATAGCTTAGCCTATAGGTGTGGGTTATTGACCATTATTGACCACTCCCTATTG
 892 GTGACGATACTTTCCATTACTAATCCATAACATGGCTCTTTGCCACAACTCTCTTTATTGGCTATATGCCAATACACTGTCCTTCA
 978 GAGACTGACACGGACTCTGTATTTTTACAGGATGGGGTCTCATTTATTATTTACAAATTCACATATACAACACCACCGTCCCCAGT
1064 GCCCGCAGTTTTTATTAAACATAACGTGGGATCTCCACGCGAATCTGGGGTACGTGTTCCGGAACGGTGGAGGGCAGTGTAGTCTG
1150 AGCAGTACTCGTTGCTGCCGCGCGCGCCACCAGACATAATAGCTGACAGACTAACAGACTGTTCCTTTCCATGGGTCTTTTCTGCA
                                   BamHI(1253)BamHI(1267)
                                   Multiple Cloning Site
         splice acceptor(1236)     NotI(1259)
1236 G TCACCGTCCT TGACACG GGATCCGCGGCCGCGGATCCCTGCCCGGGTGGCATCCCTGTGACCCCTCCCCAGTGCC
                                   BamHI   NotI  BamH              polyadenylation site (1359)
1312 TCTCCTGGTCGTGGAAGGTGCTACTCCAGTGCCCACCCAGCCTTGTCCTAATAAAATTAAGTTGCATCATTTTGT
1386 TTGACTAGGTGTCCTTGTATAATATTATGGGGTGGAGGCGGGTGGTATGGAGCAAGGGGCAGGTTGGGAAGACA
1460 ACCTGTAGGGCCTTCAGGGTCTATTGGGAACCAGGCTGGAGTGCAGTGGCACGATCTTGGCTCGCTGCAATCTC
1534 CGCCTCCTGGGTTCAAGCGATTCTCCTGCCTCAGTGTCCCGAATAGTTGGGATTCCAGGCATGCACGACCAGGC
1608 TCAGCTAATTTTTGTATTTTTGGTAGAGACGGGGTTTCACCATATTGGCCAGTCTGGTCTCCATCTCCTGACCT
1682 CAGGTAATCCGCCCGCCTCGGCCTCCCAAATTGCTGGGATTACAGGTATGAGCCACTGGGCCCTTCCCTGTCCT
1756 GTGATTTTAAAATAATTATACCAGCAGAAGGACGTCCAGACACAGCATGGGCTACCTGGCCATGCCCAGCCAGT
                                                                           SalI(1873)
                                                    SV40 early promoter/enhancer (1868)
                                                    EcoRI(1867)
1830 TGGACATTTGAGTTGTTTGCTTGGCACTGTCCTCTCATGAATTCGTCGACAGATCTGCGCAGCACCATGGCCTGAAATAA
1910 CCTCTGAAAGAGGAACTTGGTTAGGTACCTTCTGACGCGGAAAGAACCAGCTGTGGAATGTGTGTCAGTTAGGGTGTGGAAAGTCC
1996 CCAGGCTCCCCAGCAGGCAGAAGTATGCAAAGCATGCATCTCAATTAGTCAGCAACCAGGTGTGGAAAGTCCCCAGGCTCCCCAGC
2002 AGGCAGAAGTATGCAAAGCATGCATCTCAATTAGTCAGCAACCATAGTCCCGCCCCTAACTCCGCCCATCCCGCCCCTAACTCCGC
2168 CCAGTTCCGCCCATTCTCCGCCCCATGGCTGACTAATTTTTTTTATTTATGCAGAGGCCGAGGCCGCCTCGGCCTCTGAGCTATTC
                                                              HindIII (2298)
2254 CAGAAGTAGTGAGGAGGCTTTTTTGGAGGCCTAGGCTTTTGCAAAAAGCTTGATTCTTCTGACACAACAGTCTCGAACTTAAGCTG
2340 CAGAAGTTGGTCGTGAGGCACTGGGCAGGTAAGTATCAAGGTTACAAGACAGGTTTAAGGAGACCAATAGAAACTGGGCTTGTCGA
2426 GACAGAGAAGACTCTTGCGTTTCTGATAGGCACCTATTGGTCTTACTGACATCCACTTTGCCTTTCTCTCCACAGGTGTCCACTCC
                                                                       DHFR coding sequence (2568)
2512 CAGTTCAATTACAGCTCTTAAGGCTAGAGTACTTAATACGACTCACTATAGGctagcATGGTTCGACCATTGAACTGCATCG
2594 TCGCCGTGTCCCAAAATATGGGGATTGGCAAGAACCGAGACCTACCCTGGCCTCGCTCAGGAACGAGTTCAAG
2668 TACTTCCAAAGAATGACCACAACCTCTTCAGTGGAAGGTAAACAGAATCTGGTGATTATGGGTAGGAAAACCTG
2742 GTTCTCCATTCCTGAGAAGAATCGACCTTTAAAGGACAGAATTAATATAGTTCTCAGTAGAGAACTCAAAGAAC
2816 CACCACGAGGAGCTCATTTTCTTGCCAAAAGTTTGGATGATGCCTTAAGACTTATTGAACAACCGGAATTGGCA
2990 AGTAAAGTAGACATGGTTTGGATAGTCGGAGGCAGTTCTGTTTACCAGGAAGCCATGAATCAACCAGGCCACCT
2964 CAGACTCTTTGTGACAAGGATCATGCAGGAATTTGAAAGTGACACGTTTTTCCCAGAAATTGATTTGGGGAAAT
3038 ATAAACTTCTCCCAGAATACCCAGGCGTCCTCTCTGAGGTCCAGGAGGAAAAAGGCATCAAGTATAAGTTTGAA
         EcoRI (3137)           SalI (3161)
3112 GTCTACGAGAAGAAAGACTAACTCGAGAATTCACGCGTGGTACCTCTAGAGTCGACCCCGGGCGGCCGGCCGCTTCGAGCAGAC
```

FIG. 11B-1

```
3195 ATGATAAGATACATTGATGAGTTTGGACAAACCACAACTAGAATGCAGTGAAAAAAATGCTTTATTTGTGAAATTTGTGATGCTAT
                          polyadenylation site (3308)
3281 TGCTTTATTTGTAACCATTATAAGCTGCAATAAACAAGTTAACAACAACAATTGCATTCATTTTATGTTTCAGGTTCAGGGGGAGG
                                                                               EcoRI (3433)
                                                           SalI (3427)
3367 TGTGGGAGGTTTTTTAAAGCAAGTAAAACCTCTACAAATGTGGTAAAATCGATAAGGATCTGTCGACGAATTCACTGGCCGTCGTT
3453 TTACAACGTCGTGACTGGGAAAACCCTGGCGTTACCCAACTTAATCGCCTTGCAGCACATCCCCCTTTCGCCAGCTGGCGTAATAG
3539 CGAAGAGGCCCGCACCGATCGCCCTTCCCAACAGTTGCGCAGCCTGAATGGCGAATGGCGCCTGATGCGGTATTTTCTCCTTACGC
3625 ATCTGTGCGGTATTTCACACCGCATATGGTGCACTCTCAGTACAATCTGCTCTGATGCCGCATAGTTAAGCCAGCCCCGACACCCG
3711 CCAACACCCGCTGACGCGCCCTGACGGGCTTGTCTCCTCCCGGCATCCGCTTACAGACAAGCTGTGACCGTCTCCGGGAGCTGCAT
3797 GTGTCAGAGGTTTTCACCGTCATCACCGAAACGCGCGAGACGAAAGGGCCTCGTGATACGCCTATTTTTATAGGTTAATGTCATGA
3883 TAATAATGGTTTCTTAGACGTCAGGTGGCACTTTTCGGGGAAATGTGCGCGGAACCCCTATTTGTTTATTTTTCTAAATACATTCA
3969 AATATGTATCCGCTCATGAGACAATAACCCTGATAAATGCTTCAATAATATTGAAAAAGGAAGAGTATGAGTATTCAACATTTCCG
4055 TGTCGCCCTTATTCCCTTTTTTGCGGCATTTTGCCTTCCTGTTTTTGCTCACCCAGAAACGCTGGTGAAAGTAAAAGATGCTGAAG
4141 ATCAGTTGGGTGCACGAGTGGGTTACATCGAACTGGATCTCAACAGCGGTAAGATCCTTGAGAGTTTTCGCCCCGAAGAACGTTTT
4227 CCAATGATGAGCACTTTTAAAGTTCTGCTATGTGGCGCGGTATTATCCCGTATTGACGCCGGGCAAGAGCAACTCGGTCGCCGCAT
4313 ACACTATTCTCAGAATGACTTGGTTGAGTACTCACCAGTCACAGAAAAGCATCTTACGGATGGCATGACAGTAAGAGAATTATGCA
4399 GTGCTGCCATAACCATGAGTGATAACACTGCGGCCAACTTACTTCTGACAACGATCGGAGGACCGAAGGAGCTAACCGCTTTTTTG
4485 CACAACATGGGGGATCATGTAACTCGCCTTGATCGTTGGGAACCGGAGCTGAATGAAGCCATACCAAACGACGAGCGTGACACCAC
4571 GATGCCTGTAGCAATGGCAACAACGTTGCGCAAACTATTAACTGGCGAACTACTTACTCTAGCTTCCCGGCAACAATTAATAGACT
4657 GGATGGAGGCGGATAAAGTTGCAGGACCACTTCTGCGCTCGGCCCTTCCGGCTGGCTGGTTTATTGCTGATAAATCTGGAGCCGGT
4743 GAGCGTGGGTCTCGCGGTATCATTGCAGCACTGGGGCCAGATGGTAAGCCCTCCCGTATCGTAGTTATCTACACGACGGGGAGTCA
4829 GGCAACTATGGATGAACGAAATAGACAGATCGCTGAGATAGGTGCCTCACTGATTAAGCATTGGTAACTGTCAGACCAAGTTTACT
4915 CATATATACTTTAGATTGATTTAAAACTTCATTTTTAATTTAAAAGGATCTAGGTGAAGATCCTTTTTGATAATCTCATGACCAAA
5001 ATCCCTTAACGTGAGTTTTCGTTCCACTGAGCGTCAGACCCCGTAGAAAAGATCAAAGGATCTTCTTGAGATCCTTTTTTTCTGCG
5087 CGTAATCTGCTGCTTGCAAACAAAAAAACCACCGCTACCAGCGGTTGTTTGTTTGCCGGATCAAGAGCTACCAACTCTTTTTCCGA
5173 AGGTAACTGGCTTCAGCAGAGCGCAGATACCAAATACTGTCCTTCTAGTGTAGCCGTAGTTAGGCCACCACTTCAAGAACTCTGTA
5259 GCACCGCCTACATACCTCGCTCTGCTAATCCTGTTACCAGTGGCTGCTGCCAGTGGCGATAAGTCGTGTCTTACCGGGTTGGACTC
5345 AAGACGATAGTTACCGGATAAGGCGCAGCGGTCGGGCTGAACGGGGGGTTCGTGCACACAGCCCAGCTTGGAGCGAACGACCTACA
5431 CCGAACTGAGATACCTACAGCGTGAGCTATGAGAAAGCGCCACGCTTCCCGAAGGGAGAAAGGCGGACAGGTATCCGGTAAGCGGC
5517 AGGGTCGGAACAGGAGAGCGCACGAGGGAGCTTCCAGGGGGAAACGCCTGGTATCTTTATAGTCCTGTCGGGTTTCGCCACCTCTG
5603 ACTTGAGCGTCGATTTTTGTGATGCTCGTCAGGGGGGCGGAGCCTATGGAAAAACGCCAGCAACGCGGCCTTTTTACGGTTCCTGG
5689 CCTTTTGCTGGCCTTTTGCTCACATGTTCTTTCCTGCGTTATCCCCTGATTCTGTGGATAACCGTATTACCGCCTTTGAGTGAGC
5775 GATACCGCTCGCCGCAGCCGAACGACCGAGCGCAGCGAGTCAGTGAGCGAGGAAGCGGAAGAGCGCCCAATACGCAAACCGCCTCT
5861 CCCCGCGCGTTGGCCGATTCATTAATGCAGCTGGCACGACAGGTTTCCCGACTGGAAAGCGGGCAGTGAGCGCAACGCAATTAATG
5947 TGAGTTAGCTCACTCATTAGGCACCCCAGGCTTTACACTTTATGCTTCCGGCTCGTATGTTGTGTGGAATTGTGAGCGGATAACAA
6033 TTTCACACAGGAAACAGCTATGACCATGATTACGCCA
```

FIG. 11B-2

```
2660 bp DNA linear (SEQ ID NO:18)
DEFINITION Homo sapiens growth hormone variant precursor (GH-V) gene, complete cds.
ACCESSION K00470 VERSION K00470.1 GI:183174
sig peptide join(556..565,837..904) /gene="GH-V"
mat peptide join(905..997,1208..1327,1419..1583,1834..2028) /gene="GH-V"
/product="growth hormone variant"
exon 837..997 /gene="GH-V" /number=2
exon 1208..1327 /gene="GH-V" /number=3
exon 1419..1583 /gene="GH-V" /number=4
exon 1834..2136 /gene="GH-V" /number=5
PolyA signal 2118..2123 /gene="GH-V"
repeat region 2234..2505 /rpt_family="Alu" BASE COUNT 593 a 719 c 753 g 595 t
gaattcagca ctgaatcatg cccagaaccc ccgcaatcta ttggctgtgc tttggcccct   61
tttcccaaca cacacattct gtctggtggg tggaggggaa acatgcgggg aggaggaaag  121
gaataggata gagagtggga tggggtcggt aggggtctca aggactggcc tatcctgaca  181
tccttctccg cgttcaggtt ggccaccatg gcctgctgcc agagggcacc cacgtgaccc  241
ttaaagagag gacaagttgg gtggtatctc tggctgacat tctgtgcaca accctcacaa  301
cgctggtgat ggtgggaagg gaaagatgac aagtcagggg gcatgatccc agcatgtgtg  361
ggaggagctt ctaaattatc cattagcaca agcccgtcag tggccccagg cctaaacatg  421
cagagaaaca ggtgaggaga agcagcgaga gagaaggggc aggtatataaa aagggcccac  481
aagagaccag ctcaaggatc ccaaggccca actccccgaa ccactcaggg tcctgtggac  541
agctcactag cggcaatggc tgcaggtaag cgcccctaaa atccctttgg cacaatgtgt  601
cctgagggga gaggcggcgt cctgtagatg ggacggggc actaaccctc aggtttgggg  661
cttatgaatg ttagctatcg ccatctaagc ccagtatttg gccaatctct gaatgttcct  721
ggtccctgga ggaggcagag agagagagag agaaaaaaaa aacccagctc ctggaacagg  781
gagagcgctg gcctcttgct ctccagctcc ctctgttgcc tccggtttct ccccaggctc  841
ccggacgtcc ctgctcctgg cttttggcct gctctgcctg tcctggcttc aagagggcag  901
tgccttccca accattccct tatccaggct ttttgacaac gctatgctcc gcgcccgtcg  961
cctgtaccag ctggcatatg acacctatca ggagtttgta agctcttggg taatgggtgc 1021
gcttcagagg tggcaggaag gggtgaattt ccccgctgg gaagtaatgg gaggagacta 1081
aggagctcag ggttgttttc tgaagtgaaa atgcaggcag atgagcatac gctgagtgag 1141
gttcccagaa aagtaacaat gggagcaggt ctccagcata gaccttggtg ggcggtcctt 1201
ctcctaggaa gaagcctata tcctgaagga gcagaagtat tcattcctgc agaaccccca 1261
gacctccctc tgcttctcag agtctattcc aacaccttcc aacagggtga aaacgcagca 1321
gaaatctgtg agtggatgcc ttctccccag gtgggatggg gtagacctgt ggtcagagcc 1381
cccgggcagc acagccactg ccggtccttc cctgcagaa cctagagctg ctccgcatct 1441
ccctgctgct catccagtca tggctggagc ccgtgcagct cctcaggagc gtcttcgcca 1501
acagcctggt gtatggcgcc tcggacagca cgtctatcg ccacctgaag gacctagagg 1561
aaggcatcca aacgctgatg tgggtgaggg tggcaccagg atccaatcct ggggccccac 1621
tggcttccag ggactgggga gagaaacact gctgccctct ttagcagt caggcgctga 1681
cccaagagaa ctcaccgtat tcttcatttc cctcgtgaa tcctccaggc ctttctctac 1741
aacctggagg ggaggggagga aaatggatga atgagagagg gagggaacag tgcccaagcg 1801
cttggcctct ccttctcttc cttcactttg cagaggctgg aagatggcag cccccggact 1861
gggcagatct tcaatcagtc ctacagcaag tttgacacaa aatcgcacaa cgatgacgca 1921
ctgctcaaga actacgggct gctctactgc ttcaggaagg acatggacaa ggtcgagaca 1981
ttcctgcgca tcgtgcagtg ccgctctgtg gagggcagct gtggcttcta gctgcccggg 2041
tggcatccct gtgacccctc ccagtgcct ctcctggtcg tggaaggtgc tactccagtg 2101
cccaccagcc ttgtcctaat aaaattaagt tgcatcattt tgtttgacta ggtgtccttg 2161
tataatatta tggggtggag gcggtggta tggagcaagg gccaggttg gaagacaac 2221
ctgtagggcc ttcagggtct attcgggaac caggctgag tgcagtggca gtcttggctc 2281
gctgcaatct ccgcctcctg ggttcaagcg attctcctgc ctcagtctcc cgaatagttg 2341
cgattccagg catgcaagac caggctcagc taattttttgt attttttggta gagacggggt 2401
ttcaccatat tggccagtct ggtctccatc tcctgacctc aggtaatccg cccgcctcgg 2461
cctcccaaat tgctgggatt acaggtatga gccactgggc ccttccctgt cctgtgattt 2521
taaaataatt ataccagcag aaggacgtcc agacacagca tgggctacct ggccatgccc 2581
agccagttgg acatttgagt tgtttgcttg gcactgtcct ctcatgcatt gggtccactc 2641
agtagatgct tgttgaattc
```

FIG. 15

EXPRESSION CASSETTE AND VECTOR FOR TRANSIENT OR STABLE EXPRESSION OF EXOGENOUS MOLECULES

This application is the National Stage of International Application No. PCT/US2004/004407, filed Feb. 13, 2004, which claims priority to U.S. Application No. 60/448,179, filed Feb. 14, 2003.

TECHNICAL FIELD

This invention relates to expression vectors and expression cassettes, and more particularly to methods, compositions, and systems for expression of an exogenous molecule in an organism.

BACKGROUND

The introduction of nucleic acid molecules, polypeptide, peptides, and small molecules into target cells and tissues is being used both as a therapeutic delivery system as well as in the production of therapeutic molecules in vitro. The applicability of this approach has increased with the further understanding of host cells and the molecular bio logy of cell division, differentiation, and expression mechanisms.

SUMMARY

It has been discovered that transcription driven by a CMV promoter and terminated by a polyA domain from a variant human growth hormone (hGHv) gene is more efficient than other expression vectors lacking one or the other or both such elements. Therefore, the invention provides an expression cassette and an expression vector useful in the expression of polynucleotides of interest. The expression cassette of the invention includes a combination of regulatory elements that provide efficient transcription, efficient transcription termination, and increased mRNA stability of transcribed products. In one embodiment, the expression cassette includes a human cytomegalovirus promoter/enhancer, a cloning site or polynucleotide of interest, and a hGHv polyadenylation signal domain. Optionally a variable length intervening sequence may be present.

The invention provides an expression cassette that includes a human CMV immediate early 1 (hCMV IE1) promoter/enhancer region, a polynucleotide of interest, and a variant human growth hormone (hGHv) polyA signal domain or variant thereof. The polyA signal variant is at least 100 nucleotides in length and contains the sequence AATAAA, and is at least 92% identical to a hGH polyA signal domain.

The invention further provides an expression vector that includes an expression cassette of the invention as well as host cells containing a expression cassette or expression vector of the invention.

The invention further provides an expression cassette that includes a human CMV immediate early 1 (hCMV IE1) promoter/enhancer region, a variable length intervening sequence (VLIVS) comprising a splice donor and splice acceptor site, a polynucleotide of interest, and a variant human growth hormone (hGHv) polyA signal domain or variant thereof. The polyA signal domain or variant thereof is at least 100 nucleotides in length and contains the sequence AATAAA and is at least 92% identical to a hGHv polyA signal domain.

The invention also provides an expression vector that includes a human CMV immediate early 1 (HCMV IE1) promoter/enhancer region, a variable length intervening sequence (VLIVS) comprising a splice donor site and a splice acceptor site, a cloning site, a hGH poly adenylation region, and a selectable marker. In one aspect of the invention, the hCMV IE1 promoter/enhancer region is upstream (5') to the cloning site and the hGH poly adenylation region is downstream (3') to the cloning site.

The invention also includes a method of delivering an agent of interest in vivo. The method includes delivering a composition comprising an expression cassette to a subject, the expression cassette includes a hCMV IE1 promoter/enhancer region; a variable length intervening sequence comprising a splice donor and splice acceptor site; a polynucleotide encoding the agent of interest; and a human growth hormone (hGH) polyA signal domain or variant thereof The invention further includes an expression system. The expression system includes a host cell transfected or transformed with an expression cassette of the invention, wherein the host cell is cultured under conditions to express the polynucleotide of interest; and recovering the agent of interest.

The details of one or more embodiments of the invention are set forth in the accompanying drawings and the description below. Other features, objects, and advantages of the invention will be apparent from the description and drawings, and from the claims. All references cited herein are incorporated by reference.

DESCRIPTION OF DRAWINGS

FIGS. 11A and 11B are schematic representations of the vector pV90 and the corresponding annotated sequences. FIG. 11A is a vector map. Indicated are cytomegalovirus immediate early 1 (CMV IE1) promoter/intron (IVS) fragment including the splice donor (SD) and the splice acceptor (SA) sites, a hGHv polyadenylation signal domain (polyA), the ampicillin resistance gene, beta lactamase (bla), the SV40 promoter/enhancer, the artificial intron and the SV40 late polyadenylation sequence. The vector lacks the NotI site in the dhfr expression cassette. FIG. 11B is the annotated sequence of the pV90 vector. In FIG. 11B, the sequence from nucleotides 1275 to 1866 of SEQ ID NO:19 represents a hGHv polyA of about 600 nucleotides in length.

FIG. 15 shows a sequence in GenBank Accession No. K00470 (SEQ ID NO:18).

DETAILED DESCRIPTION

Figure 1:
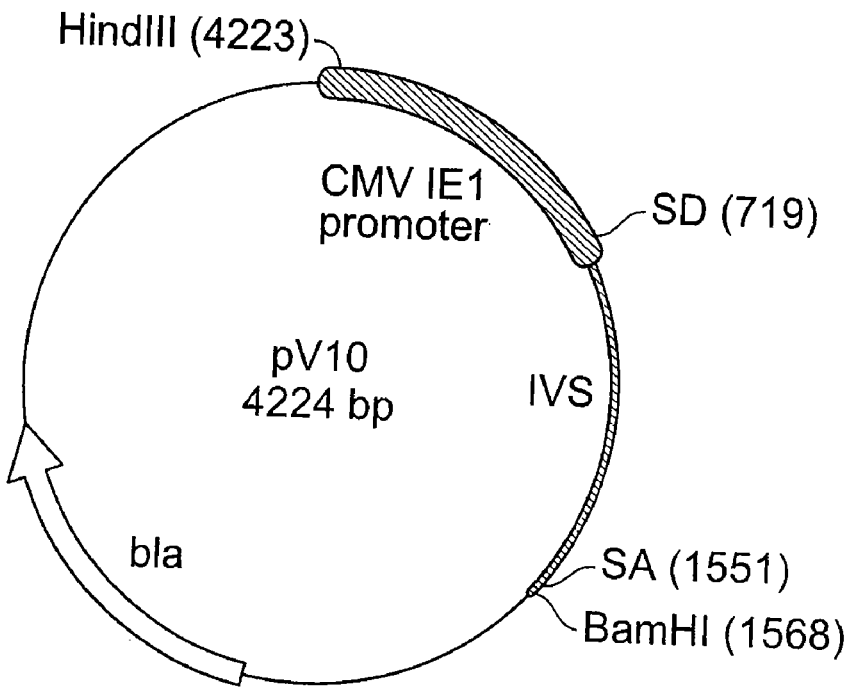
FIG. 1 is a plasmid map of the pV10 vector. The cytomegalovirus immediate early 1 (CMV IE1) promoter/intron (IVS) was generated by PCR and cloned into the HindIII and BamH1 sites. The ampicillin resistance gene, beta lactamase (bla), is also indicated.

The invention relates to an expression cassette and vectors containing the expression cassettes The expression cassette includes a transcriptional regulatory region capable of driving transcription in a eukaryotic host and a transcriptional termination region. The expression cassettes and vectors of the invention provide for a strong transcription start and stop as well as increased mRNA stability of transcribed products.

The invention provides promoter and optionally enhancer elements from any strain of cytomegalovirus, such as described herein or in references such as U.S. Pat. No. 5,658, 759, the disclosure of which is incorporated herein by reference. For example, suitable CMV immediate early promoter regions useful in the expression cassettes of the invention can be obtained from the CMV-promoted β-galactosidase expression vector, CMVβ(MacGregor et al., Nucl. Acids Res. 17:2365 (1989)).

As discussed further herein, the hGHv polyadenylation signal domain provides a strong transcriptional stop signal as well as increases the stability of the mRNA transcript. The regulatory/expression element may be separated from the hGHv polyadenylation signal domain by, for example, a polynucleotide of interest or a cloning site (e.g., a multiple cloning site).

In one aspect of the invention, there is provided a polynucleotide comprising an expression cassette that includes a cytomegalovirus (CMV) transcriptional regulatory region, a variable length intervening sequence (e.g., from intron A of CMV), a polynucleotide of interest, and a polyadenylation signal domain. The invention further relates to processes and expression vectors for producing and recovering heterologous polypeptides from host cells.

In another aspect, an expression cassette of the invention includes, operably linked, (i) a CMV major immediate early 1 (IE1) promoter/enhancer region and a variable length intervening sequence (e.g., derivative of intron A), (ii) a polynucleotide of interest, and (iii) a hGHv polyadenylation signal domain. The term "operably linked" refers to a juxtaposition wherein the components are in a relationship permitting them to function in their intended manner (e.g., functionally linked). Thus, for example, a promoter/enhancer operably linked to a polynucleotide of interest is ligated to the latter in such a way that expression of the polynucleotide of interest is achieved under conditions which are compatible with the activation of expression from the promoter/enhancer.

In a specific embodiment of the invention, the expression cassette includes a sequence as set forth in SEQ ID NO:1 from about nucleotide 1 to about nucleotide 1867 (e.g., from about 1 to 1865, 1866, 1867, 1868, or 1869). The expression cassette set forth from nucleotide 1 to 1867 of SEQ ID NO:1 includes a number of distinct domains such as a CMV IE1 promoter/enhancer region having a sequence as set forth from about $x_1$ to about $x_2$ of SEQ ID NO:1, wherein $x_1$ is a nucleotide from 1-20 and $x_2$ is a nucleotide from about 715-720 (e.g., from about 1 to 719 of SEQ ID NO:1). Another domain of the expression cassette includes a variable length intervening sequence (VLIVS) containing a splice donor and a splice acceptor site. The VLIVS can be at least 50 bp in length (e.g., at least 100, 150, 200, or 250 bp in length) and can include splice donors and acceptors from any source known in the art. See, e.g., Varani et al., Annu Rev Biophys Biomol Struct 27:407-45 (1998) and Koning, Eur J Biochem 219:25-42 (1994). A suitable intervening domain can include all of intron A of a CMV genome of any strain or may include a smaller fragment comprising a 5' sequence containing a splice donor site ligated to a 3' sequence containing a splice acceptor site. For example, the VLIVS includes nucleotides from about $x_3$ to about $x_4$ of SEQ ID NO:1, wherein $x_3$ is a nucleotide from 715-720 and $x_4$ is a nucleotide from 1236-1254 (e.g., 719 to 1236 of SEQ ID NO:1). The intervening sequence following the CMV IE1 promoter/enhancer can vary in size as much as 317 nucleotides from that present in SEQ ID NO:1. For example, 317 nucleotides were deleted from the IVS sequence as depicted in pV40 and pV70 (see, e.g., FIGS. 2 and 3, respectively) to produce the VLIVS of SEQ ID NO:1. Thus, in another aspect of the invention the expression cassette includes a sequence from about nucleotide 1 to about 1254 of SEQ ID NO:1 (e.g., a CMV IE1 promoter/enhancer and an intervening sequence). A multiple cloning site may be present after (i.e., downstream of) the IVS region (e.g., nucleotides 1255-1272 of SEQ ID NO:1 includes BamH1 sites and a Not1 site). Different or additional restriction sites may be engineered in the expression cassette using techniques known to those of skill in the art. The expression cassette further includes a polyA domain.

The polyA signal domain is derived from a hGHv gene, which can vary in its 3'UTR sequence, e.g., from allele to allele. One allele of the hGHv gene is described in GenBank Accession No. K00470 (SEQ ID NO:18), while another sequence is described in FIG. 11B as SEQ ID NO:19, which corresponds to nucleotides 2032 to 2625 of SEQ ID NO:18 (See FIG. 15). Non-naturally occurring variants of the polyA signal domain may be made by mutagenesis techniques, including those applied to polynucleotides, cells or organisms. A polyA variant from a hGHv gene includes polyA signal domain that varies from a wild-type hGHv polyA signal domain yet retains the ability to signal transcriptional termination and/or stabilize mRNA. For example, the polyadenylation signal domain may include an hGHv polyadenylation signal domain sequence as set forth in SEQ ID NOs:18 or 19. One skilled in the art of molecular biology will also understand that the sequences need not be as long as about 600 nucleotides. Rather, any polyA sequence domain that includes a contiguous nucleotide sequence of at least 100 nt (e.g., at least 200, 300, 400, 500, or 600 nt), including the canonical AATAAA site, of a hGHv gene is included. In addition, the invention encompasses sequences that vary from the foregoing sequences by up to 8% (e.g., have 92% identity to SEQ ID NO:18 or 19 or a distinct domain thereof). For example, a polynucleotide of 100 nt in length having 95% identity to nucleotides 1-1867 of SEQ ID NO:1 and including the sequence AATAAA would retain the ability to terminate transcription.

In another aspect of the invention a vector comprising an expression cassette is provided. As used herein, a "vector" is a nucleic acid molecule (either DNA or RNA) capable of autonomous replication upon introduction into a recipient cell (e.g., a bacterium such as E. coli). Plasmids, viruses and bacteriophages are examples of vectors. The process of "expression" from an expression vector is well known, and includes the use of cellular enzymes and processes to produce an expression product from a polynucleotide of interest. Expression vectors are vectors that are capable of mediating the expression of a cloned polynucleotide in a host cell, which may or may not be the same type of cell used for replication or propagation of the vector. Many mammalian expression vectors can be propagated in common bacteria (recipient cell) but express the polynucleotide of interest in mammalian cells (host cell) and not in bacterium.

The invention concerns the design and use of vectors that are capable of permitting efficient transcription and translation of polynucleotides in eukaryotic (e.g., mammalian, and most particularly, human, murine, simian, bovine, porcine, rodent, or ovine cells) cells. The vectors of the invention include an expression cassette as set forth above including a polyadenylation signal domain that provides for efficient transcriptional termination and mRNA stability.

The vectors of the invention include: a cloning site for receiving a polynucleotide of interest; transcription regulatory elements (e.g., CMV IE1 promoter/enhancer regions) sufficient to permit transcription of a polynucleotide inserted into the cloning site in a host cell; translation elements sufficient to permit translation of an RNA transcript of said polynucleotide in a host cell and (if desired) replication elements sufficient to permit the replication of said vector in a host cell or another recipient cell used for propagation of the vector. The vectors of the invention are capable of mediating such expression transiently or stably in host cells.

In a specific embodiment a vector of the invention includes (1) a sequence as set forth in SEQ ID NO:1; (2) a sequence that is complementary to the sequence as set forth in SEQ ID NO:1; (3) a sequence that is at least 80% (preferably at least 90%; 95%; 98% or 99%) identical to SEQ ID NO:1 or its complement; or (4) a vector comprising SEQ ID NO:1 from about nucleotide 1 to about nucleotide 1867 and comprising a polynucleotide of interest and/or a selectable marker.

The vector comprising SEQ ID NO:1 has a number of distinct domains and coding regions. For example, a CMV IE1 promoter/enhancer region having a sequence as set forth from about $x_1$ to about $x_2$ of SEQ ID NO:1, wherein $x_1$ is a nucleotide from 1-20 and $x_2$ is a nucleotide from about 715-720 (e.g., from about 1 to 719 of SEQ ID NO:1) is present in the vector. Another domain of an expression vector of the invention includes a variable length intervening sequence (VLIVS) containing a splice donor and splice acceptor site. For example, the IVS includes nucleotides from about $x_3$ to about $x_4$ of SEQ ID NO:1, wherein $x_3$ includes a nucleotide from 715-720 and $x_4$ includes a nucleotide from 1236-1254 (e.g., about nucleotides 719 to 1236 of SEQ ID NO:1). A multiple cloning site of the expression vector includes nucleotides 1255-1272 of SEQ ID NO:1 (e.g., BamH1 sites and a Not1 site). Different or additional restriction sites may be engineered in the expression vector using techniques known to those of skill in the art. The expression vector further includes a polyA signal domain. The polyA signal domain is a hGHv polyA signal domain or other variant of the hGH polyA signal domain. For example, a polyA signal domain includes an hGHv polyA signal domain sequence as set forth in SEQ ID NO:19. Also present in a vector of the invention is one or more selectable markers. For example, SEQ ID NO:1 includes a dihydrofolate reductase (dhfr) gene (e.g., from about nucleotide 2568 to about nucleotide 3132 of SEQ ID NO:1). A vector of the invention may include additional promoter/enhancer elements and regulatory regions (e.g., polyadenylation domains) in addition to those provided above. Such additional regulatory elements and polyadenylation domains may flank (e.g., be immediately adjacent to, 5' and 3' of) a selectable marker or polynucleotide of interest. For example, the vector comprising SEQ ID NO:1 contains a dihydrofolate reductase (dhfr) gene from about nucleotide 2568 to about nucleotide 3132 of SEQ ID NO:1. The dhfr gene is flanked by an SV40 promoter/enhancer element and an SV40 polyadenylation region (e.g., about nucleotide 1868 to about nucleotide 2210 and about nucleotide 3144 to about nucleotide 3440 of SEQ ID NO:1, respectively).

Specific examples of selectable markers are those that encode proteins that confer resistance to cytostatic or cytocidal drugs, such as the DHFR protein, which confers resistance to methotrexate (Wigler et al., Proc. Natl. Acad. Sci. USA 77:3567 (1980); O'Hare et al., Proc. Natl. Acad. Sci. USA 78:1527 (1981)); the GPF protein, which confers resistance to mycophenolic acid (Mulligan & Berg, Proc. Natl. Acad. Sci. USA 78:2072 (1981)), the neomycin resistance marker, which confers resistance to the aminoglycoside G-418 (Colbere-Garapin et al., J. Mol. Biol. 150:1 (1981)); the Hygro protein, which confers resistance to hygromycin (Santerre et al., Gene 30:147 (1984)); and the Zeocin™ resistance marker (available commercially from Invitrogen). In addition, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:2026 (1962)), and adenine phosphoribosyltransferase (Lowy et al., Cell 22:817 (1980)) can be employed in tk−, hgprt− or aprt− cells, respectively. Other selectable markers encode puromycin N-acetyl transferase or adenosine deaminase.

The terms "identical" or percent "identity," in the context of two or more nucleic acid molecules, refer to two or more sequences or subsequences that are the same or have a specified percentage of nucleotides that are the same, when compared and aligned for maximum correspondence over a comparison window, as measured using a comparison algorithm or by manual alignment and visual inspection. This definition also refers to the complement of a sequence (e.g., the complement of a sequence as set forth in SEQ ID NO:1 or a fragment thereof comprising an expression cassette). For example, the expression cassette and fragments thereof include those with a nucleotide sequence identity that is at least about 80%, about 90%, and about 95%, about 97%, about 98% or about 99% identical to a portion of SEQ ID NO:1 (e.g., nucleotides 1-719, 1-1254, and the like, of SEQ ID NO:1). Thus, if a sequence has the requisite sequence identity to the full sequence of SEQ ID NO:1 or a domain thereof then it can also function as an expression cassette or domain of the invention, respectively.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identity for the test sequence(s) relative to the reference sequence, based on the designated or default program parameters. A "comparison window", as used herein, includes reference to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, PILEUP, BESTFIT, FASTA, and TFASTA in the Wisconsin Genetics Software Package, Genetics Computer Group, 575 Science Dr., Madison, Wis.), or by manual alignment and visual inspection.

One example of an algorithm that is suitable for determining percent sequence identity (i.e., substantial similarity or identity) is the BLAST algorithm, which is described in Altschul, J. Mol. Biol. 215:403-410, 1990. Software for performing BLAST analyses is publicly available through the National Center for Biotechnology Information (on the World Wide Web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. "T" is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In one embodiment, to determine if a nucleic acid sequence is within the scope of the invention, the BLASTN program (for nucleotide sequences) is used incorporating as defaults a wordlength (W) of 11, an expectation (E) of 10, M=5, N=4, and a comparison of both strands. For amino acid sequences, the BLASTP program uses as default parameters a wordlength (W) of 3, an expectation (E) of 10, and the BLOSUM62 scoring matrix (see, e.g., Henikoff, Proc. Natl. Acad. Sci. USA 89:10915, 1989).

The BLAST algorithm also performs a statistical analysis of the similarity between two sequences (see, e.g., Karlin, Proc. Nat'l. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Also included in the invention are polynucleotides that specifically hybridize to a polynucleotide sequence as set forth in SEQ ID NO:1 from about nucleotide 1 to 1867 or a fragment thereof. The phrase "selectively (or specifically) hybridizes to" refers to the binding, duplexing, or hybridizing of a molecule to a particular reference polynucleotide under stringent hybridization conditions. The phrase "stringent hybridization conditions" refers to conditions under which a probe will primarily hybridize to its target subsequence, typically in a complex mixture of nucleic acid, but to no other sequences. Stringent conditions are sequence-dependent and will be different in different circumstances, e.g., depending on the length of the probe. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to about 50 nucleotides) and at least about 60° C. for long probes (e.g., greater than about 50 nucleotides). Stringent conditions may also be achieved with the addition of destabilizing agents such as formamide. For selective or specific hybridization, a positive signal (e.g., identification of a nucleic acid of the invention) is about 2 times background hybridization. "Stringent" hybridization conditions that are used to identify substantially identical nucleic acids Within the scope of the invention include hybridization in a buffer comprising 50% formamide, 5×SSC, and 1% SDS at a temperature between 42° C. and 65° C., with a wash of 0.2×SSC and 0.1% SDS at 65° C., for long probes. However, as is apparent to one of ordinary skill in the art, hybridization conditions can be modified depending on sequence composition. Exemplary "moderately stringent hybridization conditions" include a hybridization in a buffer of 40% formamide, 1 M NaCl, and 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Thus, an expression cassette of the invention can include a hGHv polyA signal domain that hybridizes under high stringency conditions to a ssDNA containing the nucleotide sequence of SEQ ID NO:18 or 19.

The expression cassette may be used in the form of a naked nucleic acid construct. Alternatively, the expression cassette may be introduced as part of a nucleic acid vector (e.g. an expression vector such as those described above). Such vectors include plasmids and viral vectors. A vector may include sequences flanking the expression cassette that include sequences homologous to eukaryotic genomic sequences, such as mammalian genomic sequences, or viral genomic sequences. This will allow the introduction of the expression cassette into the genome of eukaryotic cells or viruses by homologous recombination. For example, a plasmid vector comprising the expression cassette flanked by viral sequences can be used to prepare a viral vector suitable for delivering the expression cassette to a vertebrate, including fish, avian or mammalian cells. The techniques employed are well known to a skilled person.

The term "polynucleotide of interest" is intended to cover nucleic acid molecules that are capable of being at least transcribed. The molecule may be in the sense or antisense orientation with respect to the promoter. Antisense constructs can be used to inhibit the expression of a gene in a cell according to well-known techniques. The polynucleotide of interest may include a heterologous polynucleotide. The term heterologous polynucleotide encompasses any gene. A heterologous polynucleotide typically originates from a foreign species compared to the regulatory element with which it is operably linked in the expression cassette or vector or if originated from the same source, is the modified gene from its original form. Therefore, a heterologous polynucleotide operably linked to a promoter is from a source different from that from which the promoter was derived, or, if originated from the same source, is the modified promoter from its original form. Modification of the heterologous polynucleotide may occur, e.g., by treating the DNA with a restriction enzyme to generate a DNA fragment that is capable of being operably linked to the promoter. Site-directed mutagenesis is also useful for modifying a heterologous polynucleotide. Heterologous polynucleotides may also include marker genes (e.g., encoding β-galactosidase or green fluorescent protein) or genes whose products regulate the expression of other genes. Thus polynucleotides that serve as templates for mRNA, tRNA and rRNA are included within this definition. The heterologous gene may be any allelic variant of a wild-type gene, or it may be a mutant gene mRNA will optionally include some or all of 5' and/or 3' transcribed but untranslated flanking regions naturally, or otherwise, associated with the translated coding sequence.

The polynucleotide of interest may optionally further include the associated transcriptional control elements normally associated with the transcribed molecules, for example transcriptional stop signals, polyadenylation domains and downstream enhancer elements. The polynucleotide of interest can encode or serve as template for a therapeutic product, which can for example be a peptide, polypeptide, protein, or ribonucleic acid. The polynucleotide of interest is typically a DNA sequence (such as cDNA or genomic DNA) coding for a polypeptide product such as enzymes (e.g. β-galactosidase); blood derivatives; hormones; cytokines; interleukins; interferons; TNF; growth factors (e.g. IGF-1); soluble receptor molecules (e.g., soluble TNF receptor molecules); neurotransmitters or their precursors; trophic factors such as BDNF, CNTF, NGF, IGF, GMF, aFGF, bFGF, NT3 and NT5; apolipoproteins such as ApoAI and ApoAIV; dystrophin or a minidystrophin; tumor-supplessing proteins such as p53, Rb, Rap1A, DCC and k-rev; factors involved in coagulation such as factors VII, VIII and IX; or alternatively all or part of a natural or artificial immunoglobulin (eg. Fab and ScFv, or the light or heavy chain of a cloned IgG).

A polynucleotide of interest may also include a template for generation of an antisense molecule, whose transcription in a target cell enables gene expression or the transcription of cellular mRNAs to be controlled. Such molecules can, for example, be transcribed in a target cell into RNAs complementary to cellular mRNAs and can thus block their translation into proteins, according to techniques known in the art. In particular, antisense molecules can be used to block translation of inflammatory or catabolic cytokines in the treatment of arthritis and tissue loss caused by these cytokines.

The polynucleotide sequence of interest typically will encode a polypeptide of diagnostic or therapeutic use. The polypeptide may be produced in bioreactors in vitro using various host cells (e.g., COS cells or CHO cells or derivatives thereof) containing the expression cassette of the invention. Alternatively, the expression cassette and/or vector of the invention may be used for gene delivery, protein delivery, and/or gene therapy.

The invention may also be used for the expression of toxic factors and polypeptides. The latter can be, in particular, cell poisons (such as diphtheria toxin, pseudomonas toxin and ricin A), a product inducing sensitivity to an external agent (e.g. thymidine kinase and cytosine deaminase) or alternatively factors capable of inducing cell death (e.g. Grb3-3 and anti-ras ScFv).

By a therapeutic use is meant a use that may provide relief from a disease or disorder, cure a disease or disorder, and/or ameliorate the severity of a disease or disorder. A diagnostic use includes using molecules capable of determining or providing information regarding a cause or relationship of a molecule to a disease process or determining the presence or absence of a disease or disorder. A diagnostic agent does not directly contribute to the amelioration of the disease or disorder.

A polynucleotide of interest may also encode an antigenic polypeptide for use as a vaccine. Antigenic polypeptides or nucleic acid molecules are derived from pathogenic organisms such as, for example, a bacterium or a virus. For example, antigenic polypeptides include antigenic determinants present in the genomes or gene products of a pathogenic organism, for example, viral haemorrhagic septicemia, bacterial kidney disease, vibriosis, and furunculosis. Antigenic polypeptides may be selected from regions of the hepatitis C virus genome and gene products, for example.

As used herein, "isolated," when referring to a molecule or composition, such as, e.g., a vector or expression cassette of the invention, or polynucleotide of interest, means that the molecule or composition is separated from at least one other compound, such as a protein, DNA, RNA, or other contaminants with which it is associated in vivo or in its naturally occurring state. Thus, a polynucleotide of interest is considered isolated when it has been isolated from any other component with which it is naturally associated. An isolated composition can, however, also be substantially pure. An isolated composition can be in a homogeneous state. It can be in a dry/lyophilized or an aqueous solution. Purity and homogeneity can be determined, e.g., using analytical chemistry techniques such as, e.g., polyacrylamide gel electrophoresis (PAGE), agarose gel electrophoresis or high-pressure liquid chromatography (HPLC).

As used herein, the terms "nucleic acid molecule" and "polynucleotide" are used interchangeably, and include oligonucleotides (i.e., short polynucleotides). They also refer to synthetic and/or non-naturally occurring nucleic acid molecules (e.g., comprising nucleotide analogues or modified backbone residues or linkages). The terms also refer to deoxyribonucleotide or ribonucleotide oligonucleotides in either single-or double-stranded form. The terms encompass nucleic acids containing analogues of natural nucleotides. The terms also encompass nucleic acid-like structures with synthetic backbones. DNA backbone analogues provided by the invention include phosphodiester, phosphorothioate, phosphorodithioate, methyl-phosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36:8692-8698), and benzyl-phosphonate linkages (Samstag (1996) Antisense Nucleic Acid Drug Dev 6:153-156).

As used herein, "recombinant" refers to a polynucleotide synthesized or otherwise manipulated in vitro (e.g., "recombinant polynucleotide"), to methods of using recombinant polynucleotides to produce products in cells or other biological systems, or to a polypeptide ("recombinant protein") encoded by a recombinant polynucleotide. Recombinant polynucleotides encompass nucleic acid molecules from different sources ligated into an expression cassette or vector for expression of, e.g., a fusion protein; or those produced by inducible or constitutive expression of a polypeptide (e.g., an expression cassette or vector of the invention operably linked to a heterologous polynucleotide, such as a polypeptide coding sequence).

In a typical expression system, production of a polypeptide from a heterologous polynucleotide is either not regulated or is regulated by modulating transcription from a transcriptional promoter operably linked upstream of a polynucleotide that encodes the heterologous polypeptide. However, regulation must also occur properly downstream in order provide proper transcriptional termination and mRNA stability. In one aspect of the invention, a human growth hormone variant (hGHv) polyadenylation (polyA) signal domain is provided downstream (3') of a polynucleotide of interest present in an expression cassette or vector of the invention. The hGHv polyA signal domain includes a sequence derived from the human growth hormone genetic sequence. The hGHv polyadenylation signal domain sequence provides for a strong transcriptional termination and provides increased mRNA stability in eukaryotic cells. This hGHv polyadenylation signal domain provides a distinctive advantage over prior expression cassettes and/or vectors including those that may utilize a CMV promoter/enhancer.

Translation elements may also be present and are intended to encompass the specialized sequences (such as ribosome binding sites and initiation codons) that are necessary to permit translation of an RNA transcript into protein. Translation elements may also include consensus sequences, leader sequences, splice signals, and the like, that serve to facilitate or enhance the extent of translation, or increase the stability of the expressed product. For example, the hGHv polyadenylation signal domain provides increased mRNA stability. The vectors of the invention may possess ancillary transcription regions, such as introns, polyadenylation signals, Shine/Dalgarno translation signals and Kozak consensus sequences (Shine et al., Proc. Natl. Acad. Sci. (U.S.A.) 71:1342-1346 (1974); Kozak, Cell 44:283-292 (1986)).

The term "replication elements" is intended to encompass the specialized sequences (such as origins of replication) that are necessary to permit replication of the vector in a recipient cell. In general, such vectors will contain at least one origin of replication sufficient to permit the autonomous stable replication of the vector in a recipient cell.

To facilitate selection and maintenance of a vector of the invention, one or more selectable markers (such as polynucleotides that confer resistance to antibiotics, or a cellular capacity to grow on minimal medium or in the presence of toxic metabolites) may be included in the vector.

In a further embodiment, the present invention relates to host cells containing the above-described constructs (e.g., the expression cassette or vector of the invention). The expression cassette of the invention may be used to recombinantly modify a host cell by transfecting a host cell or transforming a host cell to express a desired polynucleotide of interest. As used herein, the term "recombinantly modified" means introducing an expression cassette or vector of the invention into a living cell or expression system. Usually, the expression cassette comprising a polynucleotide of interest is present in a vector (e.g., a plasmid). An expression system includes a living host cell into which a polynucleotide of interest, whose product is to be expressed, has been introduced, as described herein. 1

Host cells are cells in which an expression cassette (including a vector comprising an expression cassette) can be propagated and polynucleotides encoding products can be expressed. A host cell also includes any progeny of the subject host cell or its derivatives. It is understood that all progeny may not be identical to the parental cell since there may be mutations that occur during replication. However, such progeny are included when the term "host cell" is used. Host cells, which are useful in the invention, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein.

Host cells for use in the invention are eukaryotic host cells (e.g., mammalian cells). In one aspect of the invention the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells, which are widely used for the production of several complex recombinant proteins, e.g. cytokines, clotting factors, and antibodies (Brasel et al., Blood 88:2004-2012 (1996); Kaufman et al., J. Biol Chem 263: 6352-6362 (1988); McKinnon et al., J Mol Endocrinol 6:231-239 (1991); Wood et al., J. Immunol 145:3011-3016 (1990)). The dihydrofolate reductase (DHFR)-deficient mutant cell lines (Urlaub et al., Proc Natl Acad Sci USA 77:4216-4220 (1980)) are the CHO host cell lines of choice because the efficient DHFR selectable and amplifiable gene expression system allows high level recombinant protein expression in these cells (Kaufman, Meth Enzymol 185:527-566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies. In addition, it is contemplated that host cells derived from any of the foregoing cell lines and having a desired phenotype may also be used. For example, a derived host cell includes CHO cells (e.g., the DG44 cell line), which have been selectively cultured for a desired phenotype (e.g., by positive and/or negative selection processes).

In one aspect of the invention, an expression system for in vitro production of an agent encoded by a polynucleotide of interest is provided. As discussed herein, the polynucleotide of interest can encode a polypeptide of pharmaceutical, medicinal, nutritional, and/or industrial value. For example, the polynucleotide of interest can encode a polypeptide-based drug. Typically such a polypeptide will be expressed as an extracellular product. For example, polypeptides that may be produced using the expression cassette and/or vector of the invention include, but are not limited to, a Flt3 ligand, a CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons (e.g., interferon beta), nerve growth factors, glucagon, interleukins 1 through 18, colony stimulating factors, lymphotoxin-β, tumor necrosis factor, leukemia inhibitory factor, oncostatin-M, various ligands for cell surface molecules Elk and Hek (such as the ligands for eph-related kinases, or LERKS), and antibody light or heavy chains.

Receptors for any of the aforementioned proteins can also be expressed using the inventive methods and compositions, including both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, BAFF receptor, lymphotoxin beta receptor, TGFβ receptor types I and II, and receptors that include death domains, such as Fas or Apoptosis-Inducing Receptor (AIR).

Other proteins that can be expressed using the expression cassette and/or vectors of the invention include cluster of differentiation antigens (referred to as CD proteins), for example, those disclosed in Leukocyte Typing VI (Proceedings of the VIth International Workshop and Conference; Kishiimoto, Kikutani et al., eds.; Kobe, Japan, 1996), or CD molecules disclosed in subsequent workshops. Examples of such molecules include CD27, CD30, CD39, CD40, and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be expressed using the invention.

Polypeptides that are enzymatically active can also be expressed according to the invention. Examples include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme (TACE), and numerous other enzymes. Ligands for enzymatically active proteins can also be expressed using the cassette and vector of the invention.

The inventive compositions and methods are also useful for expression of other types of recombinant proteins and polypeptides, including immunoglobulin molecules or portions thereof and chimeric antibodies (e.g., an antibody having a human constant region coupled to a murine antigen binding region) or fragments thereof. Numerous techniques are known by which DNAs encoding immunoglobulin molecules can be manipulated to yield DNAs encoding recombinant proteins such as single chain antibodies, antibodies with enhanced affinity, or other antibody-based polypeptides (see, for example, Larrick et. al., Biotechnology 7:934-938 (1989); Reichmann et al., Nature 332:323-327 (1988); Roberts et al., Nature 328:731-734 (1987); Verhoeyen et al., Science 239: 1534-1536 (1988); Chaudhary et al., Nature 339:394-397 (1989)). Cloned humanized antibodies include those specifically binding to lymphotoxin beta receptor and integrins such as VLA-1, VLA-4, and αvβ6, Such antibodies can be agonists or antagonists.

Various fusion proteins can also be expressed using the inventive methods and compositions. Examples of such fusion proteins include proteins expressed as a fusion with a portion of an immunoglobulin molecule, proteins expressed as fusion proteins with a zipper moiety, and novel polyfunctional proteins such as a fusion proteins of a cytokine and a growth factor (e.g., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are applicable to other proteins.

Once a polynucleotide of interest is expressed, the expression product (e.g., a protein or polypeptide) may be purified using standard techniques in the art. For example, where the polynucleotide of interest encodes a fusion polypeptide comprising a purification tag, the polypeptide may be purified using antibodies that specifically bind to the tag. In one aspect an oligonucleotide encoding a tag molecule is ligated at the 5' or 3' end of a polynucleotide of interest encoding a desired polypeptide; the oligonucleotide may encode a polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as means for affinity purification of the desired polypeptide from the host cell. Affinity purification can be accomplished, for example, by column chromatography using antibodies against the tag as an affinity matrix. Optionally, the tag can subsequently be removed from the purified polypeptide by various means such as proteolytic cleavage.

The expression cassette and vectors of the invention can be used to provide a stable transfer of a polynucleotide of interest into a host cell. A stable transfer means that the polynucleotide of interest is continuously maintained in the host. The expression cassette or vector of the invention may also provide transient expression of a polynucleotide of interest in a host cell. Transiently transfected host cells lose the exogenous DNA during cell replication and growth.

An expression cassette of the invention may be used to deliver a therapeutic agent to a human or animal in need of treatment. Alternatively, the expression cassette of the invention may be used to deliver an agent encoding potentially immunogenic polypeptides in vivo for vaccine purposes to a subject (e.g., a human), particularly for vaccination of domesticated animals including animals of foodstock such as fish, porcine, equine, bovine, canine, and feline species.

The expression cassette of the invention may be administered directly as a naked nucleic acid construct, typically comprising flanking sequences homologous to a host cell genome. Uptake of naked nucleic acid constructs by vertebrate cells is enhanced by several known techniques including biolistic transformation and lipofection.

Alternatively, the expression cassette may be administered as part of a vector, including a plasmid vector or viral vector.

Typically the expression cassette or vector is combined with a pharmaceutically acceptable carrier or diluent to produce a pharmaceutical composition. Suitable carriers and diluents include isotonic saline solutions including, for example, phosphate-buffered saline. The composition comprising the expression cassette or vector can be formulated for various types of administration including, for example, intramuscular administration.

When the composition comprising the expression cassette or vector is used in an injectable form, it is typically mixed with a vehicle that is pharmaceutically acceptable for an injectable formulation for direct injection at the site to be treated. The pharmaceutically acceptable carrier or diluent may be, for example, a sterile isotonic solution. The composition comprising the expression cassette or vector may also be formulated in an orally active form.

The actual formulation used can be readily determined by the skilled person and will vary depending on the nature of the substance to be administered and the route of administration.

The dose of substance used may be adjusted according to various parameters, especially according to the substance used, the age, weight and condition of the subject to be treated, the mode of administration used and the required clinical regimen. A physician will be able to determine the required route of administration and dosage for any particular subject and condition.

EXAMPLES

Construction of pV10 Vector

Additional details of the construction of pV10 are outlined in FIG. 1. Genomic DNA was isolated from human diploid fibroblasts infected with human cytomegalovirus strain AD 169 (ATCC No. VR-538) and used as a template to PCR amplify the CMV immediate early gene 1 promoter/enhancer region (CMV IE1 P/E) (see FIG. 11(B) (SEQ ID NO:1) for details of the 5'UTR of the CMV IE1 gene). The promoter was amplified using primers containing a HindIII site at the 5' terminus (tttAAGCTTGACATTGATTATTGACTAG; SEQ ID NO:2; restriction site underlined) and a BainHI site at the 3' terminus (ttttGGATCCCTGTCAAGGACGGTGACTGC; SEQ ID NO:3; restriction site underlined). The terminal "t" nucleotides preceding the restriction site are included in the oligonucleotide design to facilitate restriction enzyme digestion and are eliminated in the cloning step.

All PCR reactions were performed in the DNA engine PTC-200 Pelier Thermal Cycler (MJ Research, Watertown, Mass.). The total reaction volume was 100 µl: IX NEB Vent polymerase buffer (10 mM KCl, 20 mM Tris pH 8.8 at 25° C., 10 mM $(NH_4)_2SO_4$, 2 mM $MgSO_4$, 0.1% Triton X-100), 2.5 mM dNTP's, 2 units Vent DNA polymerase (New England Biolabs, Beverly, Mass.), 1 µg of each primer, 1 µg of genomic DNA isolated from CMV infected cells as template.

The reaction conditions were as follows: 99° C. for 1 minute, 55° C. for 30 seconds, 75° C. for 1.5 minutes for 15 cycles. The resulting fragment was digested with restriction enzymes BainHI and HindIII (New England Biolabs) and subcloned into the cloning vector pUC 19 digested with BamHI and HindIII. The sequence analysis of the insert was determined and was consistent with the published sequence of the CMV IE1 promoter/enhancer region cloned.

Construction of pV40 Vector

Figure 2:
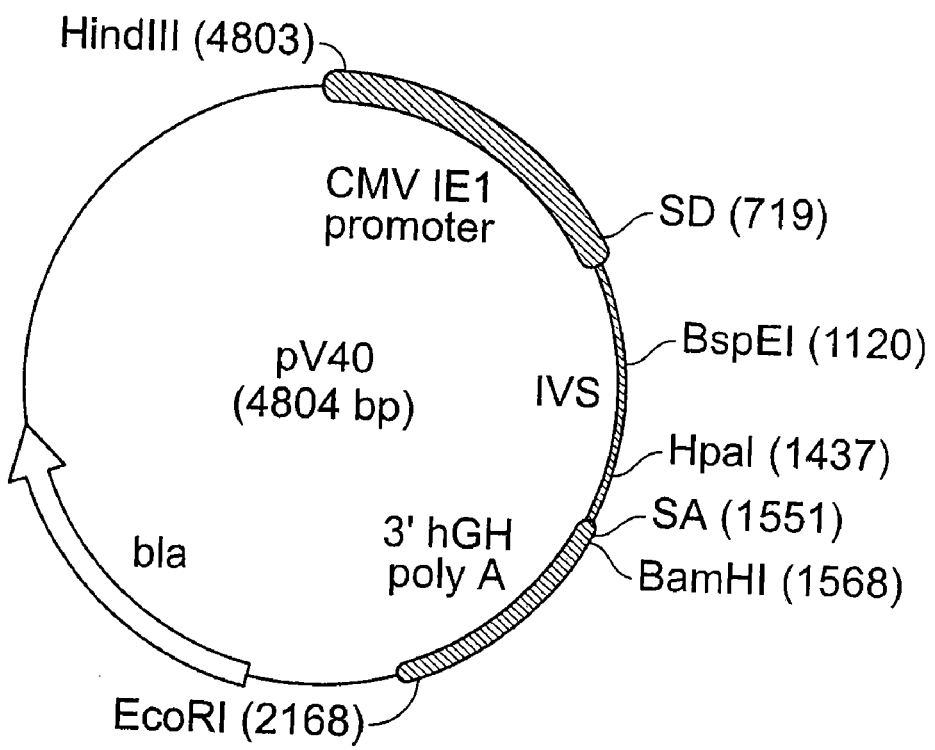
FIG. 2 is a plasmid map of pV40. Indicated are the cytomegalovirus immediate early 1 (CMV IE1) promoter, an intron (IVS), a hGHv polyadenylation signal domain (polyA) of about 600 base pairs in length, and the ampicillin resistance gene, beta lactamase (bla).

The construction of pV40 is outlined in FIG. 2. The 3'UTR of the hGHv gene including the polyA signal was PCR amplified from genomic DNA isolated from human fibroblasts. The (+) strand of 5' primer (TTTTGGATCCCTGCCCGGGTG-GCATCC; SEQ ID NO:20) contained a terminal BamHIrestriction site and the (-) strand or 3' primer contained a terminal EcoRI site (TTTTGAATTCATGAGAGGACAGT-GCCAAGC; SEQ ID NO:21). The PCR conditions were the same as described for the construction of pV10. The resulting PCR fragment was digested with BamHI and EcoRI, gel purified and ligated into vector pV10 digested with BamHI and EcoRI. The resulting plasmid, designated pV40, was verified by restriction enzyme analysis. Subsequent sequencing indicated that a small number of nucleotide differences between the 3UTR of this hGHv gene (SEQ ID NO:19) and the published hGHv gene sequence in GenBank Accession No. K00470 (SEQ ID NO:18). At least some of the changes are due to allelic variations.

Construction of pV70 Vector

The pV40 vector was digested with BspE1 and HpaI to remove a 317 nucleotide section of the Intron A region (IVS) (see, e.g., FIGS. 2 and 3). pV60 was generated by blunt end ligation into BspEI-HpaI of the dhfr coding region of pV40. The pV70 expression vector contains the human cytomegalovirus major immediate early 1 (hCMV IE1) promoter/enhancer region to regulate transcription. It also contains the hCMV IE1 5'UTR and intron A, where the intron contains a 317 base pair deletion. For the termination of transcription, the vector contains the human growth hormone variant polyadenylation (hGHv polyA) region, SEQ ID NO:19. Construction of pV40, pV60, and pV70 are detailed below and further described in the Figures.

A. Generation of pXLC.1

Figure 3:
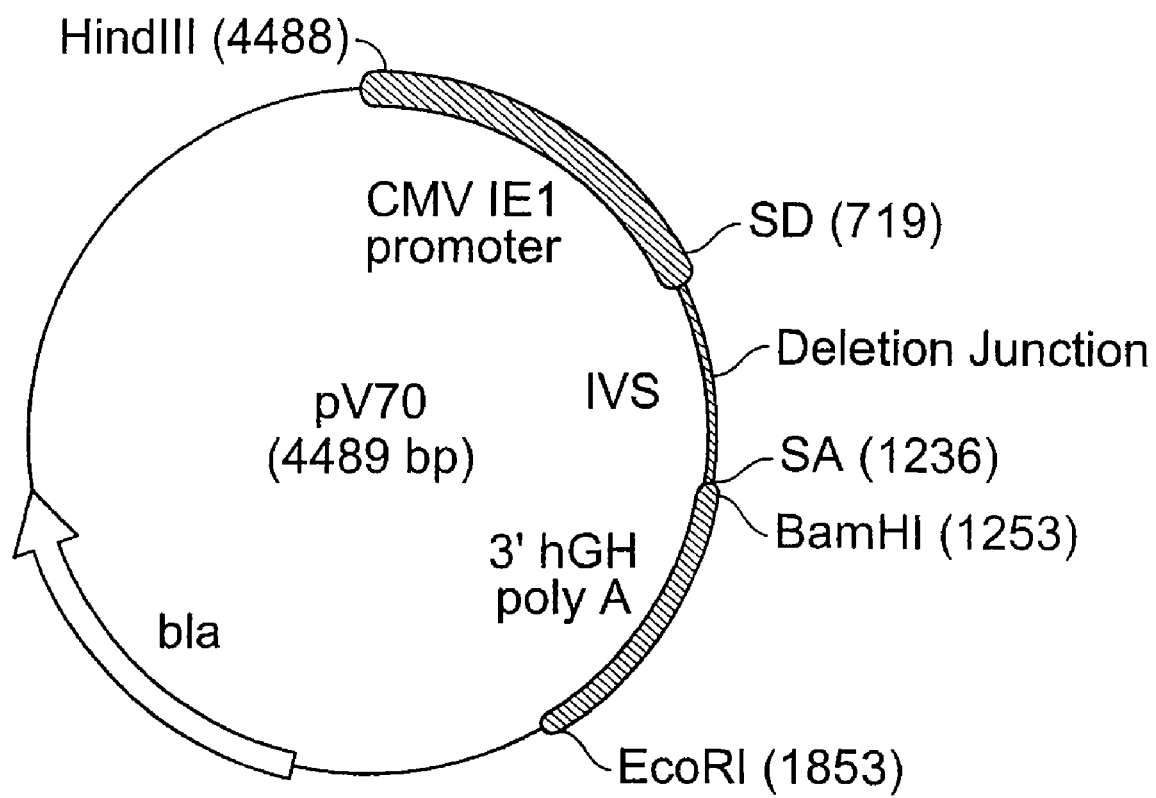
FIG. 3 is a schematic representation of the plasmid pV70. Indicated are the CMV IE1 promoter, the IVS including the deletion junction and the splice donor (SD) and splice acceptor (SA) sites, a hGHv polyA signal domain, and the bla gene. The deletion junction represents the blunt-ended ligation result of BspE1'/HpaI.
Figure 4:
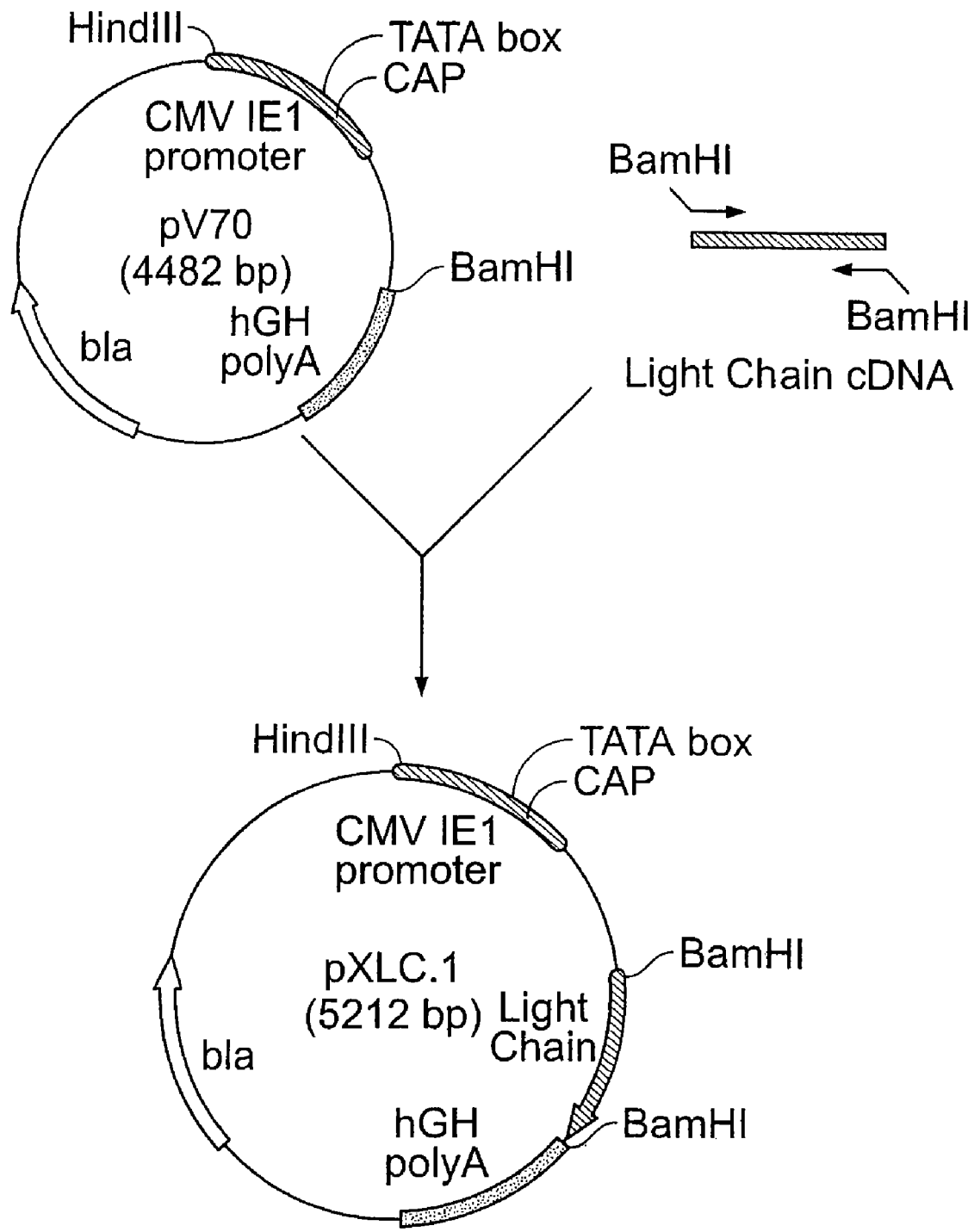
FIG. 4 is a schematic representation of the generation of the pXLC.1 vector. The pXLC.1 vector was constructed using the expression vector pV70 and a PCR product containing the light chain coding sequence. PV70 was linearized with BamHI, the PCR product was digested with BamHI and the two were ligated together to generate the pXLC.1 vector.

A PCR product containing a light chain coding sequence for an antibody was digested with BamHI and cloned into a unique BainHI site in the expression vector pV70 (FIG. 3). The light chain coding region was inserted into a unique BamHI site between the 5' UTR sequence at the 3' end of the hCMV IE1 intron and the 5' end of the hGHv poly A region. This plasmid was designated as pXLC. 1. FIG. 4 shows a schematic of the generation of the pXLC. 1 vector.

B. Addition of a Neo Cassette—pXLC.2

Figure 5:
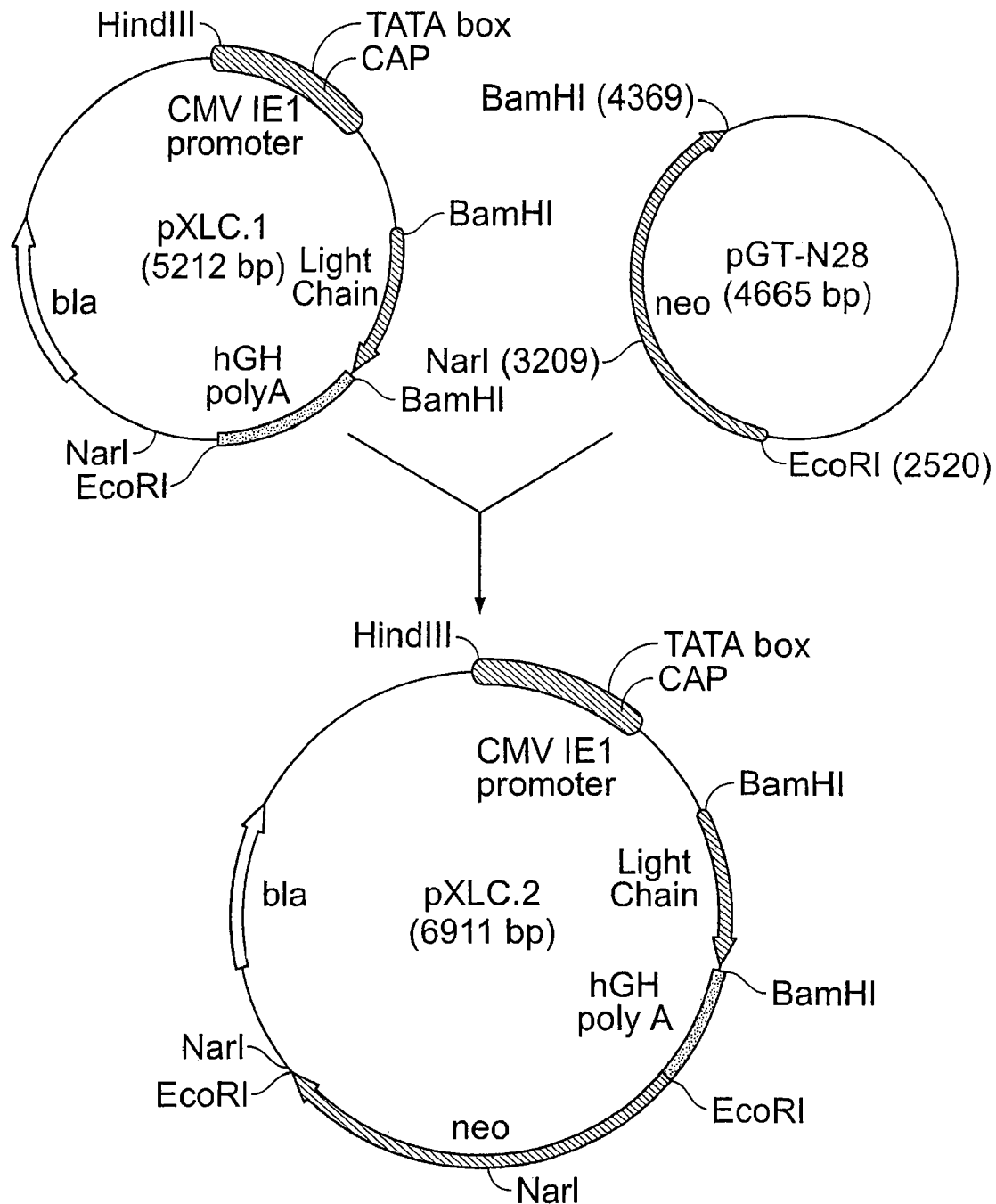
FIG. 5 is a schematic representation of the generation of the pXLC.2 vector.

A neomycin transferase (neo) expression cassette was introduced into pXLC.1 to act as a selectable marker (FIG. 5). The neo cassette was prepared as a BamHI/EcoRI fragment from a commercially available plasmid called pGT-N28 (New England Biolabs, catalog #307-28). In this plasmid, the neo gene is driven by the phosphoglycerate kinase (PGK) promoter and terminated at a PGK poly-adenylation site. The BamHI end at the 5' end of the neo cassette was converted to a NarI end using the following adaptor oligos:

```
                          EcoRI
BamHI compatible GATCGATGAATTCGG       (SEQ ID NO:4)

NarI compatible CTACTTAAGCCGC          (SEQ ID NO:5)
```

With these linkers, a new EcoRI site was also added. The adaptor was first ligated to the BamHI/EcoRI cut neo fragment, and the converted Nar/EcoRI fragment was then cloned into pXLC.1 digested with NarI and EcoRI. In this way the neo expression cassette was inserted at the 3' end of the light chain sequence of the plasmid. This plasmid was designated as pXLC.2 (FIG. 5).

Construction of the Heavy Chain Expression Vector—pXHC.5

A. RT-PCR of the Heavy Chain

The heavy chain was amplified from the RT-PCR reaction using the 5' PCR primer TTTTGGATCC ATGTACTGGGTGAAGCAG (SEQ ID NO:6), where the italicized sequence is an added linker region with a BamHI site, and the underlined bases correspond to the second methionine in the heavy chain coding sequence. The 3' PCR primer that was used, GCCCGGATC CTCATTTACCCGGAGACAG (SEQ ID NO:7), also contains an added linker region with a BamHI site (italics) and a sequence that corresponds heavy chain coding sequence including the termination codon (underlined). The expected PCR product of 1268 base pairs was obtained.

B. Construction of pXHC

Figure 6:
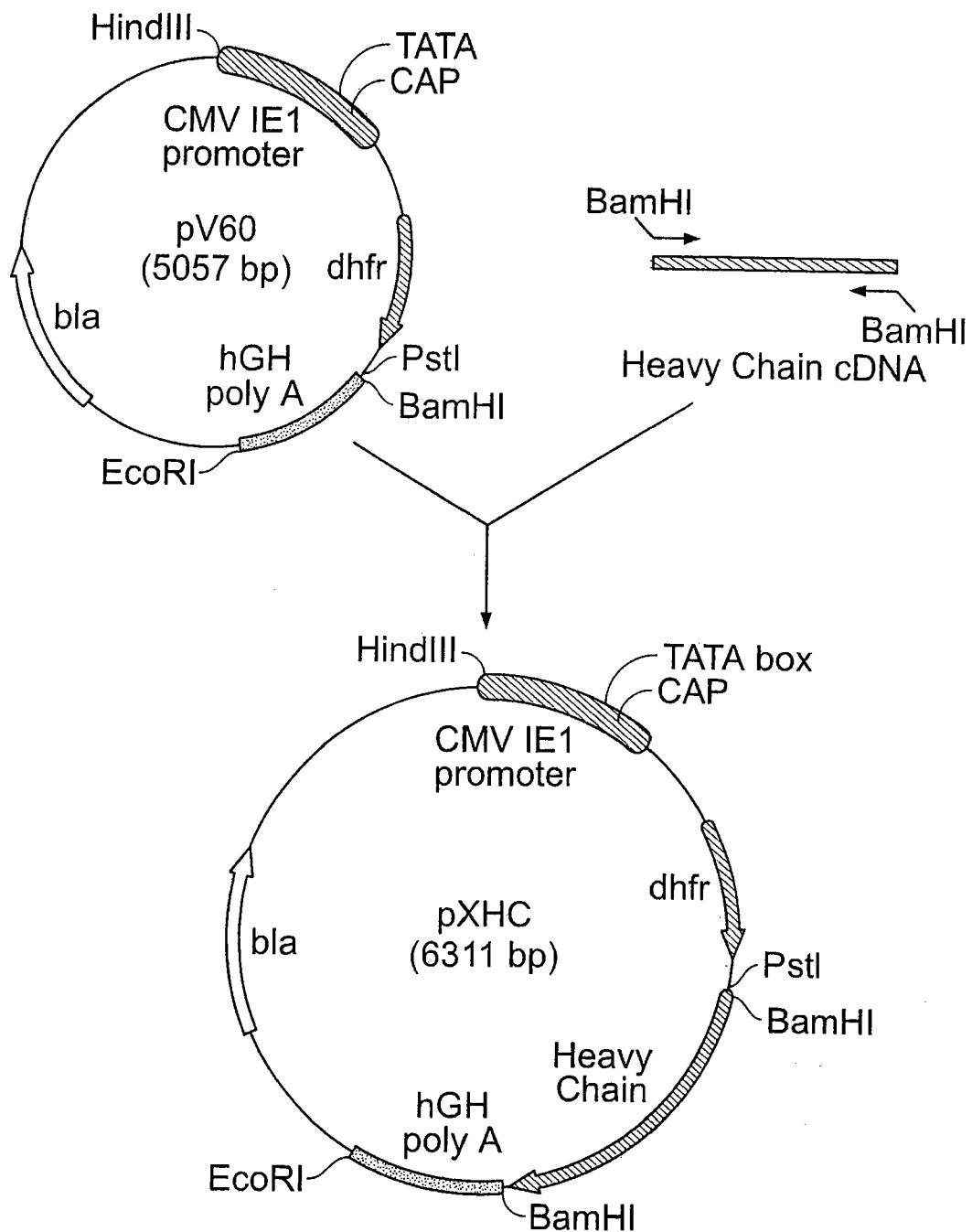
FIG. 6 is a schematic representation of a pV60 vector and the generation of the pXHC vector. The pXHC vector was constructed using the expression vector pV60 and a PCR product containing most of the heavy chain coding sequence (52 amino acids from the N-terminal were not included). PV60 was linearized with BamHI, the PCR product was digested with BamHI and the two were ligated together.

Because the 5' PCR primer used hybridized with the second ATG codon in the coding region rather than the initiation ATG the coding region contained in the PCR product, the heavy chain coding region was incomplete. The BamHI fragment, containing the incomplete heavy chain, was cloned into the plasmid pV60 (FIG. 6). This vector is identical to pV70 (described above) except that it contains the dhfr coding region at the site of the deletion in the intron. The heavy chain coding region was inserted into a unique BamHI site between the 5' untranslated sequence at the 3' end of the hCMV IE1 intron and the 5' end of the hGHv variant polyA region. This plasmid, with the incomplete heavy chain, was designated as pXHC.

C. Completion of the Heavy Chain Coding Sequence—pXHC.1

Figure 7:
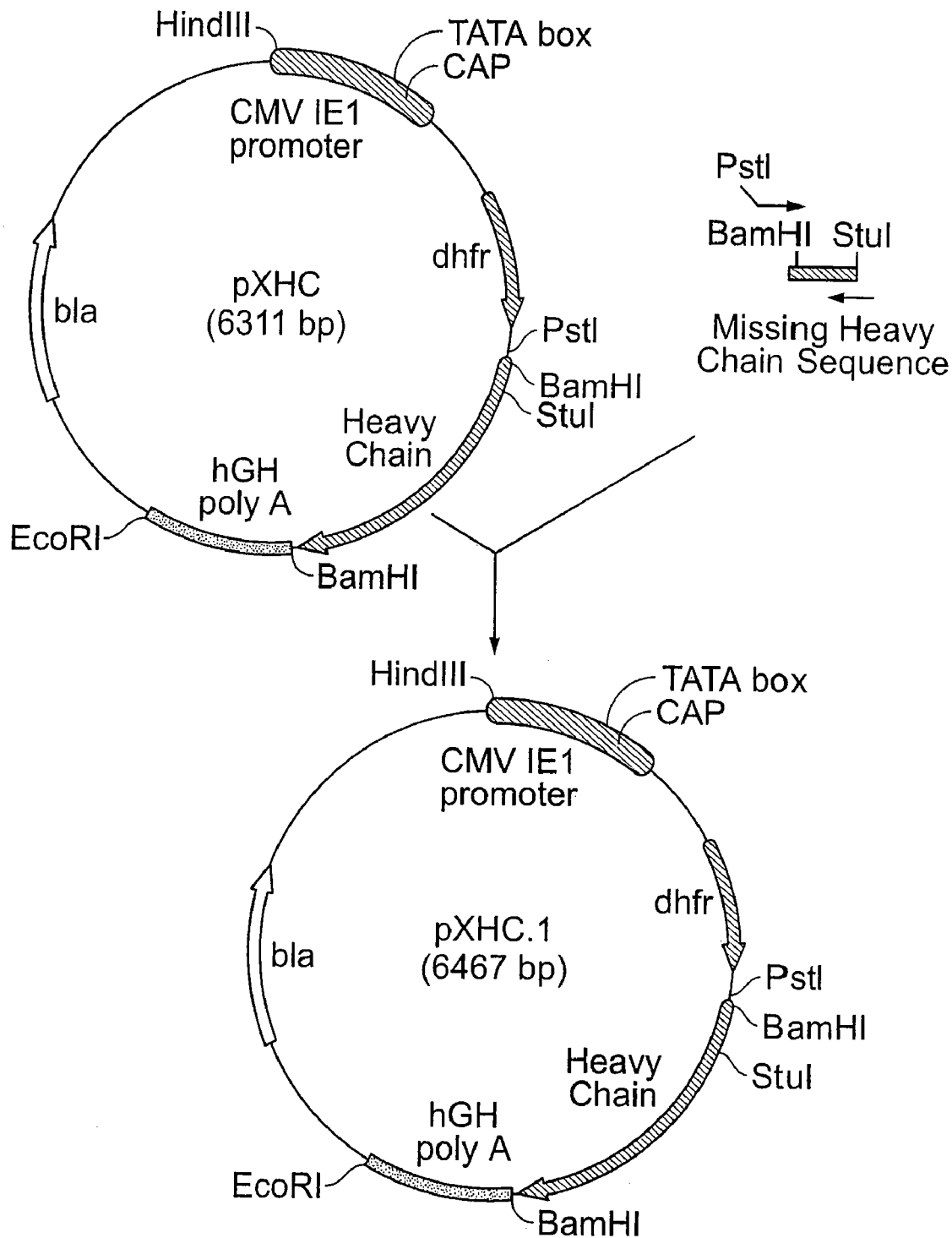
FIG. 7 is a schematic representation of a pXHC.1 vector.

The coding region that was missing from the heavy chain sequence was inserted into pXHC to generate the plasmid designated as pXHC.1 (FIG. 7). To do this, a fragment was generated by PCR using a plasmid containing the coding sequence for the antibody as a template. The 5' PCR primer used was:

was obtained as expected and cut with PstI and StuI. The PstI/StuI fragment was cloned into pXHC cut with PstI and StuI to yield pXHC.1.

Figure 8:
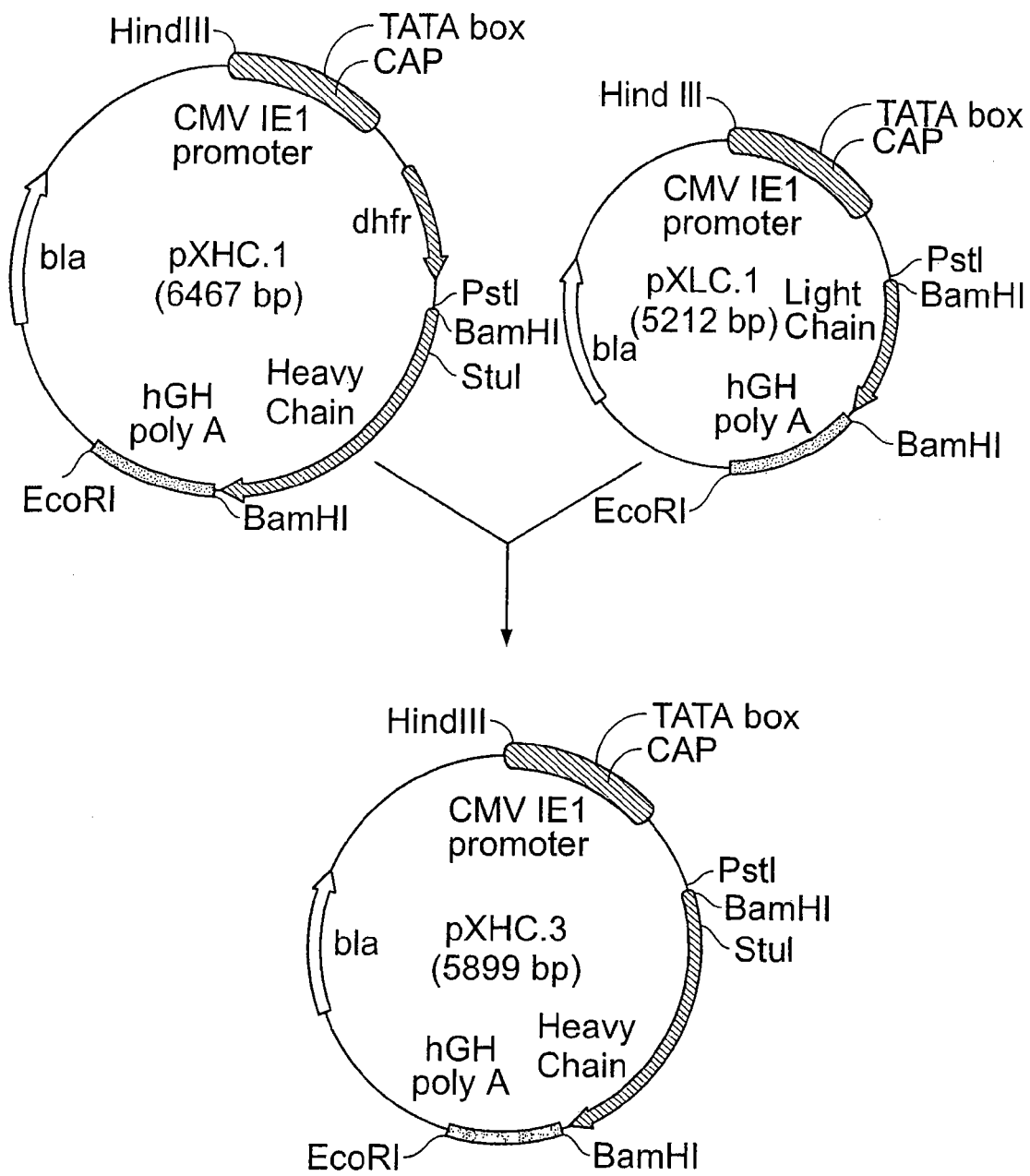
FIG. 8 is a schematic representation of a pXHC.3 vector.

D. Removal of the Intronic dhfr—pXHC.3 pXHC.1 contained a dhfr gene in the hCMV IE1 intron. Due to potential problems with amplification found with this configuration, the dhft gene was removed from the intron and an expression cassette was inserted 3' of the heavy chain cassette (FIG. 8). The first step was the removal of the dhfr gene from the intron. This was accomplished by cutting the heavy chain coding sequence out of pXHC.1 as a PstI/EcoRI fragment and cloning it into the pXLC.1 plasmid cut with the same enzymes. This cloning step simply switched the light chain for the heavy chain in the plasmid. The resulting plasmid was identical to pXHC.1 except that the intron containing the dhfr gene was replaced by an intron with a deletion as described above for pXLC.1. This heavy chain plasmid was designated as pXHC.3 (FIG. 8).

E. Insertion of the dhfr Cassette—pXHC.5

Figure 9:
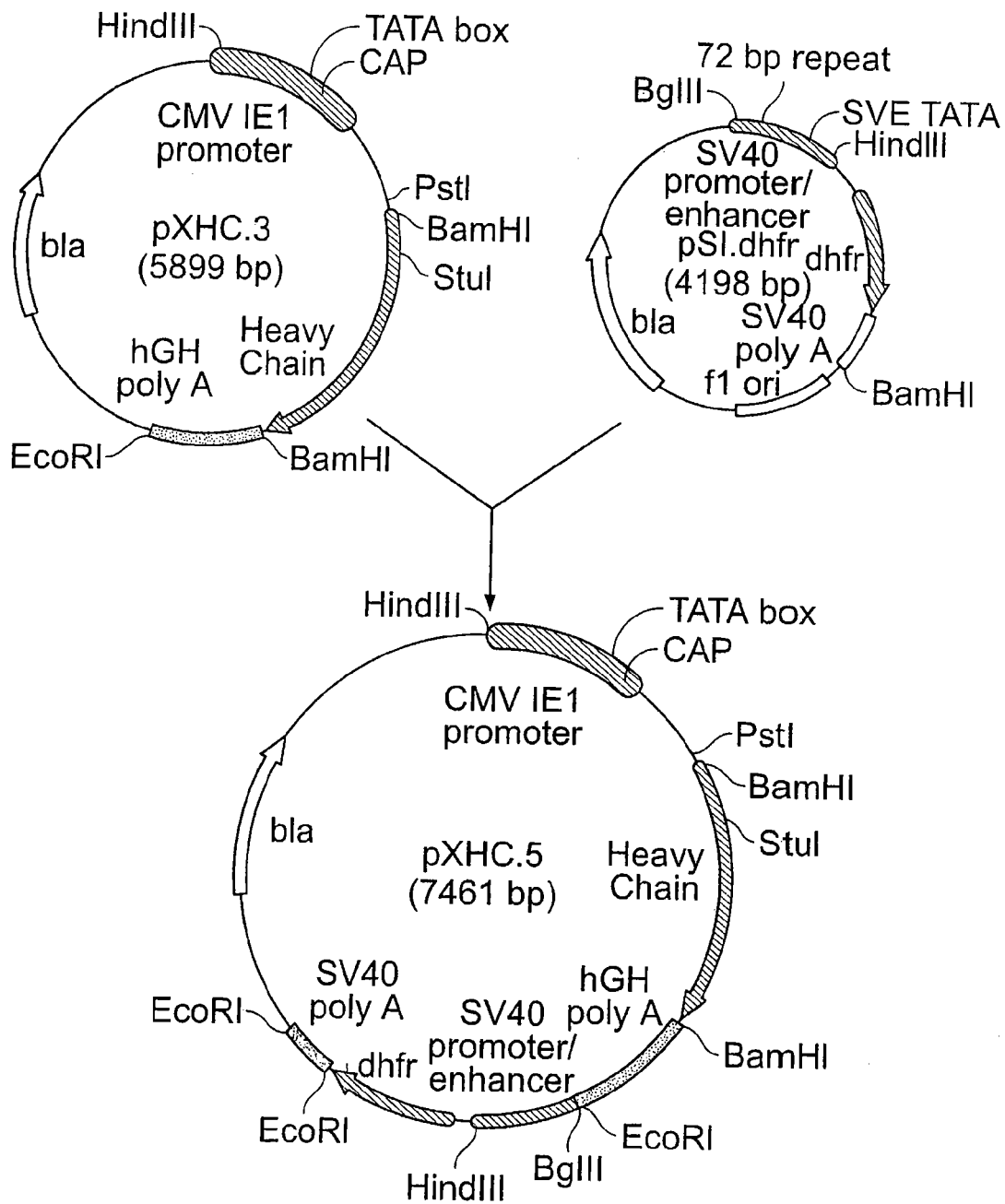
FIG. 9 is a schematic representation of a pXHC.5 vector, resulting from the addition of a dhfr cassette to pXHC.3. The control elements of the expression cassette were derived from pSI (Promega, Genbank accession #U47121) and include the SV40 promoter/enhancer, an artificial intron and the SV40 late polyadenylation sequence.

The second step in the alteration of the dhfr configuration was the insertion of the dhfr expression cassette 3' of the heavy chain expression cassette (FIG. 9). The dhfr expression cassette was derived from the plasmid pSI-DHFR on a BglII/BamHI fragment and includes an SV40 early promoter, the dhfr gene and an SV40 poly A region. This fragment was cloned into the EcoRI site located at the 3' end of the hGHv poly A region of pXHC.3 using the following adaptor oligos:

```
                                 SalI
EcoRI compatible AATTCGTCGACA            (SEQ ID NO:10)

BamHI BglII compatible GCAGCTGTCTAG      (SEQ ID NO:11)
```

This adaptor was first ligated to the EcoRI cut plasmid and then the BglII/BamHI dhfr cassette was ligated to the adapted plasmid. This plasmid was designated as pXHC.5 (FIG. 9).

Characterization of pXLC.2 and pXHC.5

Both plasmids were analyzed using restriction enzymes to confirm the presence and orientation of the inserted fragments. In addition, the coding region of the plasmids was sequenced to verify that no mutations were accumulated during the PCR or cloning steps.

The presence of a functional neo selection marker was confirmed by transfecting pXLC.2 into CHO cells and demonstrating resistance to G418. The ability to do a dual selection was demonstrated when the pXLC.2 and pXHC.5 plasmids were co-transfected into a serun free adapted DG44 CHO host. Colonies grew out from the co-transfection in a dual selection media (a—MEM 10% DFBS with 400 mg/ml

```
                                                           (SEQ ID NO:8)
    PstI                BamHI
TTTTCTGCAGTCACCGTCCTTGACACG GGATCCATGGACTGGACCTTGGAGGG.
```

The sequence in italics corresponds to the pXHC sequence 5' of theBamHI site and the sequence in bold corresponds to the sequence starting two bases before the initiation codon in the heavy chain sequence. The 3' primer used was CTGAG-GAGACGGTGACCAGGGTCCCTTGGCCCC (SEQ ID NO:9). This primer hybridizes to the end of the first exon, the heavy chain variable region. A PCR product of 445 base pairs G418). Under the same conditions, either selection alone (a—MEM or 400 mg/ml G418) was able to kill untransfected cells.

Figure 10:
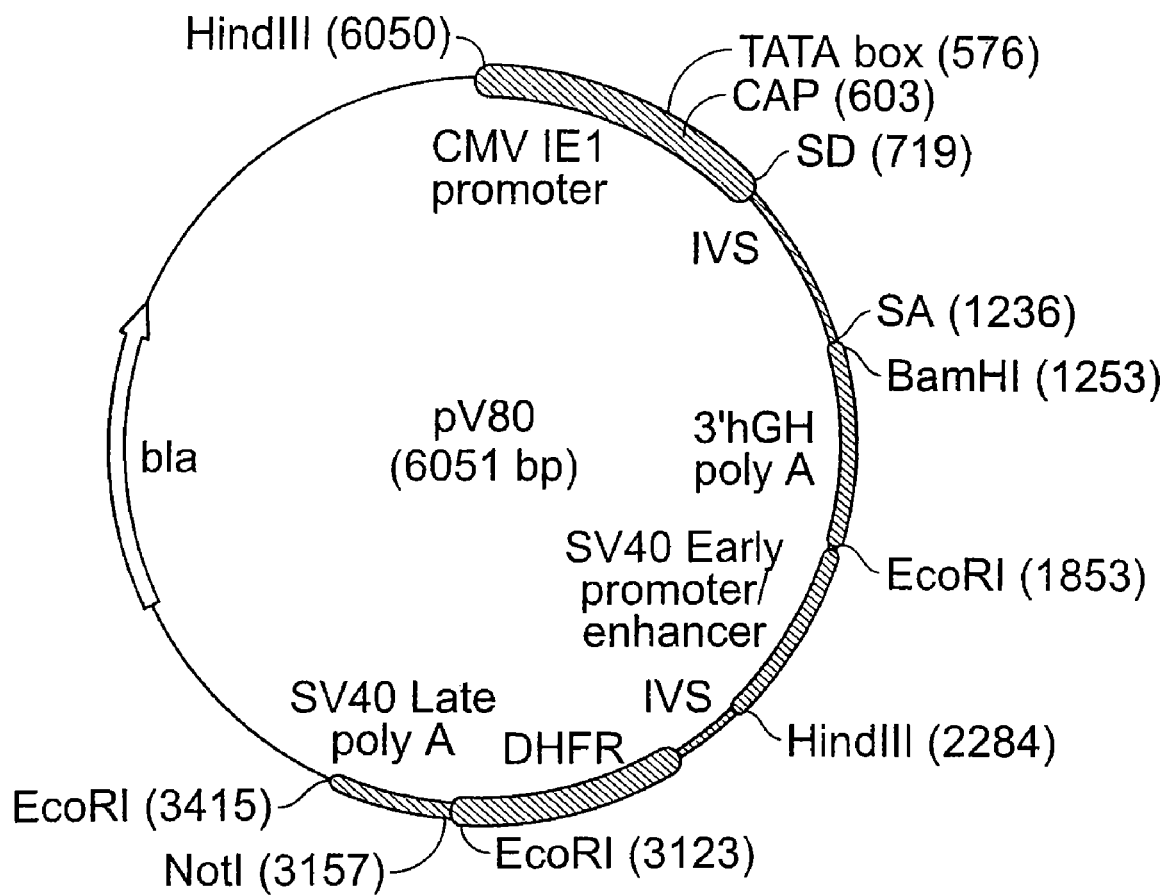
FIG. 10 is a schematic representation of the vector pV80. Indicated are the cytomegalovirus immediate early 1 (CMV IE1) promoter/intron (IVS) fragment including the splice donor (SD) and the splice acceptor (SA) sites, a hGHv polyadenylation signal domain (polyA), the ampicillin resistance gene, beta lactamase (bla), the SV40 promoter/enhancer the artificial intron and the SV40 late polyadenylation sequence.

Construction of the Vectors: pV80 and pV90 Vectors pV80 was generated from the heavy chain expression vector pXHC.5 (FIG. 10). The heavy chain coding sequence was deleted from pXHC.5 using BamHI. The backbone was ligated to re-circularize it at the BamHI site.

Figure 11A:
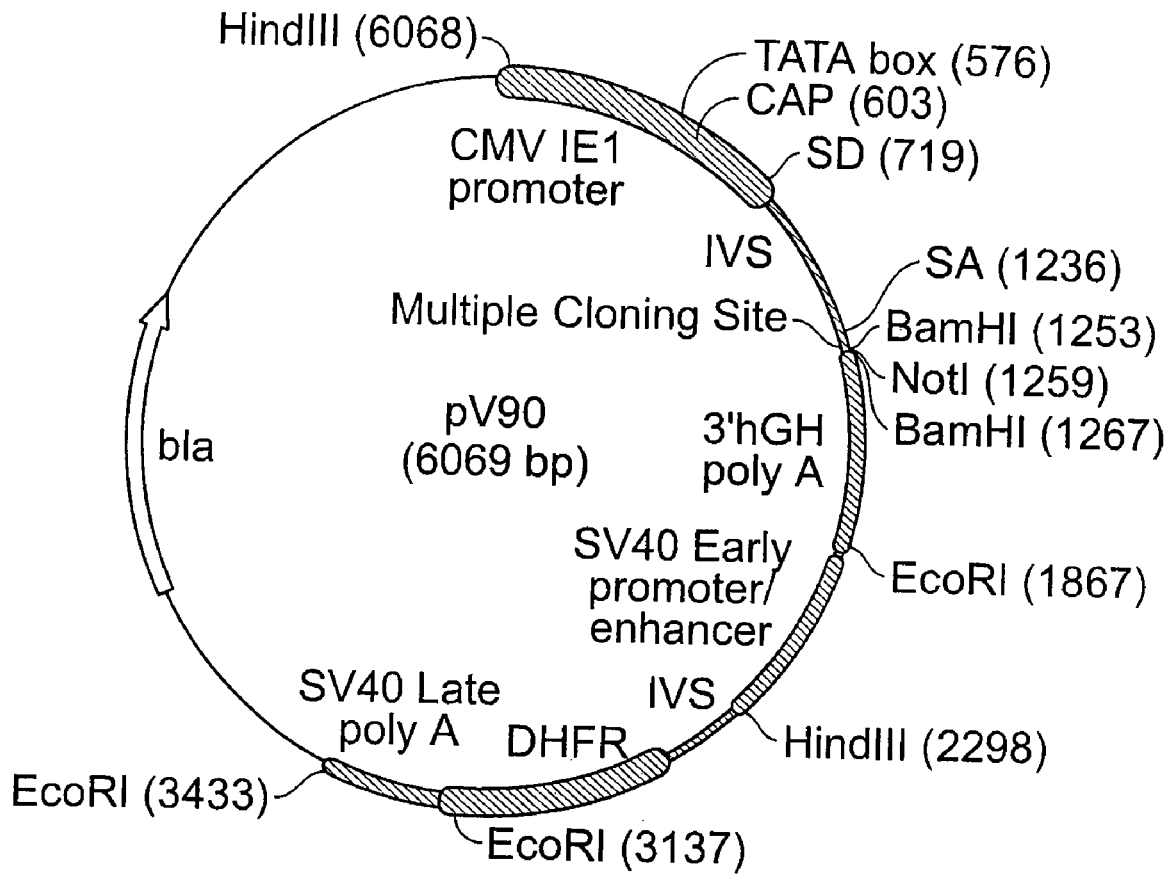

Two alterations were made to the pV80 vector to generate pV90 (FIG. 11). The Not1 site found in the pV80 construct at position 3166 (at the end of the dhfr coding region, see attached sequence) was destroyed. To accomplish this, the plasmid was digested with Not1 and the overhangs were "filled-in" using Klenow polymerase. As a result, the religated plasmid had lost the NotI site at position 3166. A new NotI site was then created at the cloning site by digesting the vector with BamHI and introducing a NotI linker made by annealing the following 14-mer with itself: GATCCGCGGC-CGCG. (SEQ ID NO:12). When annealed together, the linker sequence is:

```
                       NotI
BamHI compatible GATCCGCGGCCGC       (SEQ ID NO:13)

BamHI compatible CGCCGGCGCCTAGG      (SEQ ID NO:14)
```

This cloning step recreated BamHI sites on either side of the NotI site. These BamHI sites may be useful in the genetic analysis of stable cell lines generated with this vector. The cloning site sequence of pV90 was confirmed by sequence analysis.

In the pV80 vector a polynucleotide (e.g., a coding sequence) may be cloned into the BamHI site GGATCCCT-GCCCGGGT (SEQ ID NO:15). The bold sequence represents the BamH1 site. In the pV90 vector a polynucleotide (e.g., a coding sequence) may be cloned into the BamHI or NotI site GGATCC GCGGCCGCGGATCC CTGC-CCGGGT (SEQ ID NO:16). Here, the bold sequence represents the BamH1 site and the underlined sequence represents the Not1 site. For optimal results when using the NotI site, a "C" should be added prior to the start codon in the PCR primers to best match the Kozak sequence (e.g., GGATCC GCGGCCGC C ATG. (SEQ ID NO:17)).

Restriction Sites in pV80 and pV90 pV80 and pV90 are identical with the exception of NotI restriction sites: pV80 has a single NotI site at position 3166 (end of the dhfr coding region) and pV90 has a single NotI site at position 1260 (cloning site).

Common restriction sites of which 2 or fewer were found include those listed in Table 1.

Cloning of the Reporter Genes

The expression cassette/vector including the CMV IE1, intron A fragment, and hGHv polyA construct was compared with a commercially available SV40-based high expression vector.

Secreted alkaline phosphatase (SEAP) was used as reporter for the comparison of the plasmids. The SV40 based expression vector, pSEAP2-control (Cat # 6052-1, Clontech), expresses SEAP under the control of the SV40 early promoter and SV40 enhancer. The SEAP coding sequence is followed by the SV40 late polyadenylation signal to ensure proper, efficient processing of the SEAP transcript in eukaryotic cells. A synthetic transcription blocker (TB), composed of adjacent polyadenylation and transcription pause sites, located upstream of the MCS reduces background transcription. The vector incorporates a number of features that improve the sensitivity of SEAP by increasing the efficiency of SEAP expression or that enhance the utility of the vectors. These include: an improved Kozak consensus translation initiation site; the removal of the SV40 small-t intron, which can cause cryptic splicing and reduced expression in some genes and/or cell types; switching from the early to late polyadenylation signal of SV40, which typically causes a five-fold increase in mRNA levels; an expanded multiple cloning site (MCS); compact plasmid size; and removal of extraneous sequences from the 3' untranslated region of the SEAP mRNA. Genbank accession number U89938.

In order to generate the pCMV-hGHvPA-SEAP plasmid, the SEAP coding sequence was extracted from the pSEAP2-control plasmid by PCR and cloned into a pV110 vector. The p110 plasmid is a derivative of pV90 (no dhfr expression cassette, different polylinker, but otherwise the same). The pCMV-hGHvPA-SEAP plasmid construct was verified by sequencing.

Figure 12:
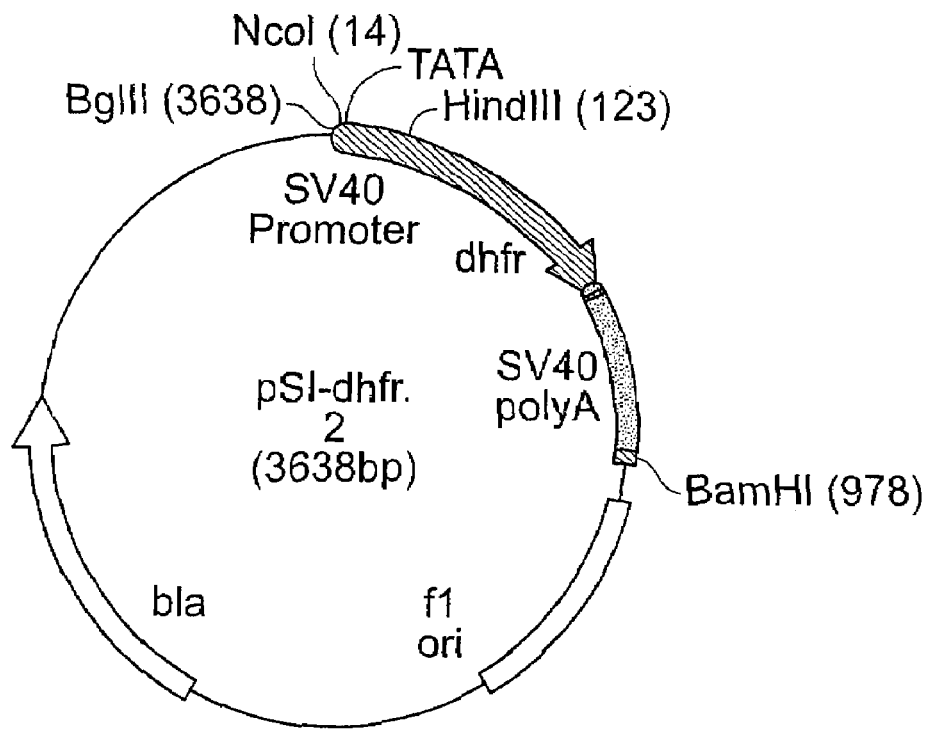
FIG. 12 is a vector map of pSI-DHFR.2. The SV40 promoter drives the dhfr gene.

The host used for transfections was the dihydrofolate reductase (DHFR) deficient Chinese hamster ovary cell line DG44 (Urlaub et al., Cell 33, 405-412 (1983)). The CMVSEAP and pSEAP2-control reporter plasmids were co-transfected with a plasmid encoding dihydrofolate reductase (dhfr) so that stable transfectants could be selected for (pSI-DHFR.2, FIG. 12). Each transfection contained 50 µg of a reporter plasmid and 5 µg pSI-DHFR.2. All DNA was prepared by Megaprep kit (Qiagen). Prior to transfection, DNA was ETOH precipitated, washed in 70% EtOH, dried, resus-

TABLE 1

| | | | |
|---|---|---|---|
| AatI (1) 2274 | ApaI (1) 1733 | AspEI (2) 1382, 4807 | BamHI (1) 1254 |
| BsgI (1) 1494 | BsiXI (1) 3404 | ClaI (1) 3404 | EgeI (1) 3585 |
| HindIII (2) 2293, 6059 | HpaI (1) 3308 | KasI (1) 3585 | Kpn2I (1) 1121 |
| KpnI (2) 1927, 3144 | NarI (1) 3585 | NdeI (2) 254, 3637 | NheI (1) 2557 |
| NotI (1) see above | PstI (2) 1231, 2331 | PvuI (2) 3544, 4440 | SacI (2) 585, 2819 |
| SacII (2) 673, 1258 | SmaI (2) 1271, 3161 | SpeI (1) 20 | StuI (1) 2274 |
| XbaI (1) 3150 | XhoI (1) 3127 | XmaI (2) 1271, 3161 | |

The following common enzyme cut sites were not found:

TABLE 2

| | | | | | | | | | | | |
|---|---|---|---|---|---|---|---|---|---|---|---|
| AatII | AfaI | AfeI | AgeI | AluI | ApaLI | AspHI | AspI | AvaI | AvaII | BsiWI | DpnI |
| DpnII | DraI | DraII | DraIII | EaeI | EagI | EarI | EcoRI | EcoRV | FspI | HaeII | HaeIII |
| HincI | HpaI | NaeI | NcoI | NdeII | NspI | PacI | SalI | SphI | XhoII | XmaIII | | pended in HEBS (20 mM Hepes, pH 7.05, 137 mM NaCl, 5 mM KC1, 0.7 mM $Na_2HPO_4$, 6 mM dextrose), and quantitated prior to transfection. Negative controls included pUC18 (ATCC No. 37253) as a reporter control and a no DNA transfection as a transfection control (Table 3).

Cells and DNA were transfected by electroporation in 0.8 ml of HEBS using a 0.4 cm cuvette (BioRad) at 0.28 kV and 950 mF. 5E6 cells were used for each transfection. After the electroporation pulse, the cells were allowed to incubate in the cuvette for 5-10 min at room temperature. They were then transferred to a centrifuge tube containing 10 ml of alpha MEM with nucleosides and 10% dFBS and pelleted at 1K RPM for 5 min. Resuspended pellets were seeded into 6-well plates in alpha MEM without nucleosides with 10% dFBS and incubated at 36° C. with 5% $CO_2$ in a humidified incubator until colonies formed.

TABLE 3

| Transfection Experiment | | |
|---|---|---|
| Reporter plasmid (50 µg each) | DHFR plasmid (5 µg each) | No. of Transfections |
| pSEAP2-control | pSIDHFR.2 | 3 |
| pCMVSEAP | pSIDHFR.2 | 3 |
| pUC18 | pSIDHFR.2 | 1 |
| No DNA | No DNA | 1 |

Approximately 2 weeks after transfection, colonies had formed in the transfections containing the pSIDHFR.2 plasmid only. Stable transfectants were analyzed as either pools or isolates. The specific productivity was assessed in assays where the medium was exchanged for fresh medium and 24 hours later the medium was sampled and the cells were counted. The product titer was normalized for the cell number at the end of the 24 hour assay, and the productivities were expressed as SEAP activity per cell.

SEAP assay. Conditioned medium was analyzed using the Great EscAPe™ SEAP Reporter System 3 (Clontech). This assay uses a fluorescent substrate to detect the SEAP activity in the conditioned medium. The kit was used in a 96 well format according to the manufacturer's instructions, with the following exceptions. The assay buffer from the kit was substituted with 1.5 M diethanolamine, 0.75 MM $MgCl_2$, 15 mM L-homoarginine, and 10% Emerald II (Cat # 9761, Applied Biosystems). All standards and samples were diluted in fresh medium rather than the dilution buffer provided. Instead of doing one reading after 60 min, multiple reads were taken at 10-20 min intervals and used to express SEAP activity as relative fluorescent units per minute (RFU/min). The emission filter used for the plate reader (Cytofluor II, PerSeptive Biosystems) was 460 nm instead of the recommended 449 nm.

The RFU/min values were normalized to a standard curve based on a standard provided with the kit. Because the standard provided was not quantitated, all values are relative. These relative values were normalized to cell numbers and the incubation period to generate relative specific productivities (SEAP activity per cell per day).

Pools. After the appearance of colonies, the cells were collected and pooled from each transfection. Pools were seeded at $\sim 2\times 10^5$ cells per well into 6-well plates. The following day the medium was exchanged for 2 ml of fresh medium. After 24 hours the cells were counted and a sample of the medium was used to assess SEAP activity. Results from the pool assays are shown in FIG. 13.

Isolates. Isolates were obtained by "picking" colonies from the transfection. "Picking" was accomplished by aspirating directly over a colony with a P200 Pipetman™ set at 50 ml. The aspirated colony was transferred first to a 48 well plate and then to a 6 well plate when there was a sufficient number of cells. Specific productivities were assessed in 6 well plates at near confluent to confluent cell densities using the 24-hour assay described above (FIG. 14).

Figure 13:
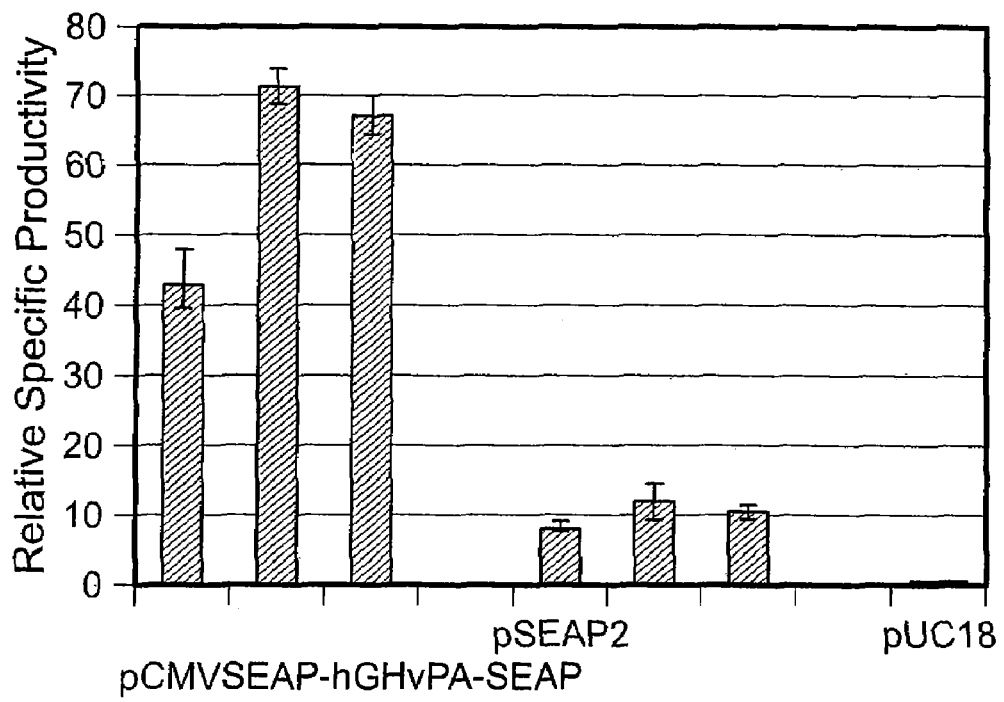
FIG. 13 is a graph depicting the relative specific productivities of the transfected pools. Three pools were analyzed for pCMV-hGHvPA-SEAP and pSEAP2, and one for pUC18.
Figure 14:
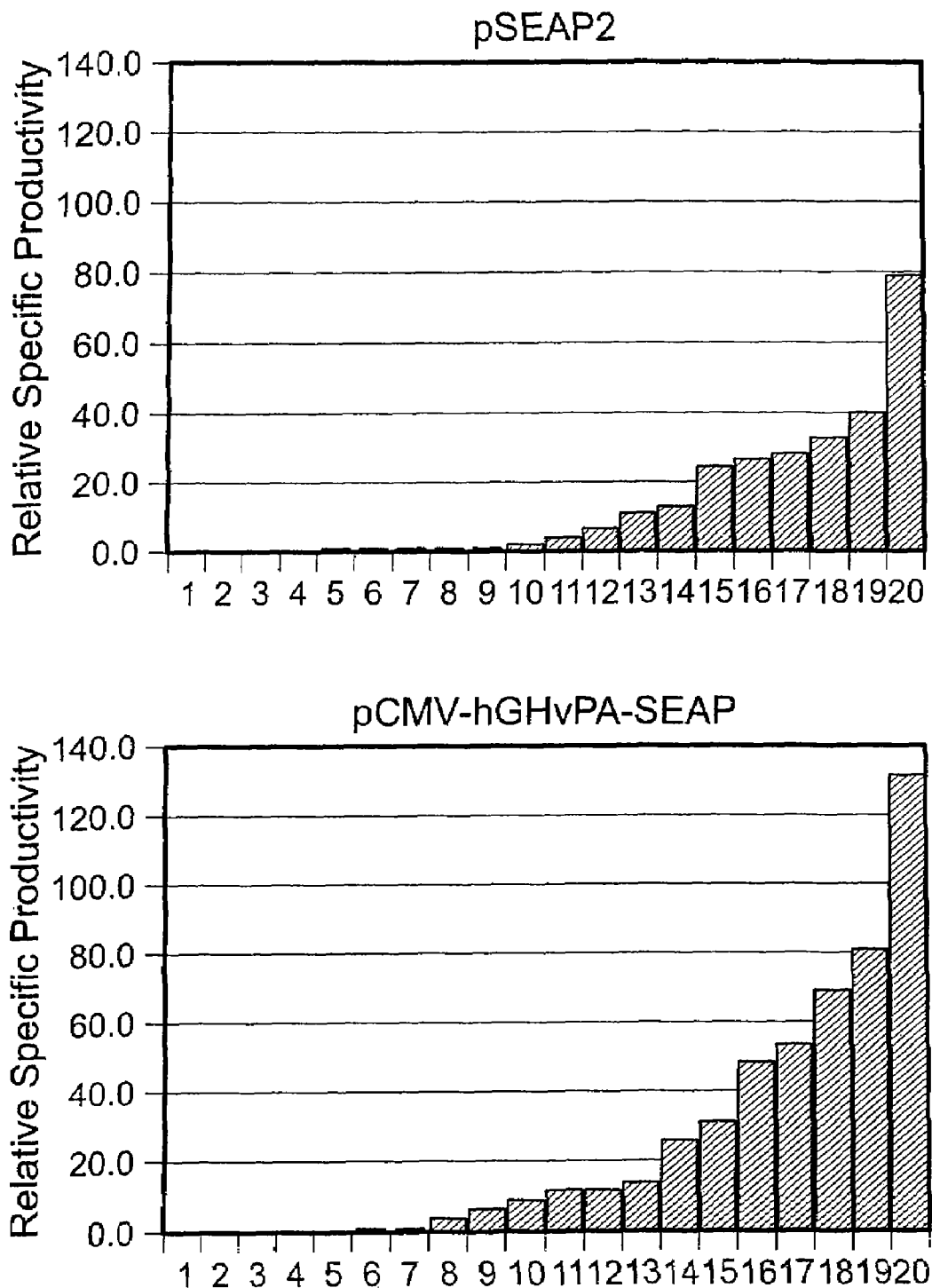
FIG. 14 is a pair of graphs showing the relative specific productivities of the isolates. The top twenty isolates from each construct are shown in rank order.

As summarized in FIGS. 13 and 14, an expression vector based on the combination of a CMV IE promoter and a hGHv polyA signal domain was far superior to a commercially available vector that boasts of high expression capabilities.

A number of embodiments of the invention have been described. Nevertheless, it will be understood that various modifications may be made without departing from the spirit and scope of the invention. Accordingly, other embodiments are within the scope of the following claims.

We claim:

1. An expression cassette comprising:
   (i) a human CMV immediate early 1 (hCMV IE1) promoter/enhancer region;
   (ii) a polynucleotide of interest;
   (iii) a variant human growth hormone (hGHv) polyA signal domain; and
   (iv) a variable length intervening seciuence (VLIVS) comprising a splice donor and splice acceptor site;
   wherein the hGHv polyA signal domain is at least 100 nucleotides in length, contains the sequence AATAAA, and is a variant of a wild-type human growth hormone polyA signal domain that is at least 92% identical to said wild-type human growth hormone polyA signal domain; and
   wherein the VLIVS comprises an intron A of a hCMV IE1 gene.

2. The expression cassette of claim 1, wherein the expression cassette comprises a sequence as set forth from about $x_1$ to about $x_2$ of SEQ ID NO:1, wherein $x_1$ denotes a nucleotide from about 1 to about 20 of SEQ ID NO:1 and $x_2$ denotes a nucleotide from about 715 to about 720 of SEQ ID NO:1.

3. The expression cassette of claim 1, wherein the expression cassette comprises the sequence as set forth in SEQ ID NO:1.

4. The expression cassette of claim 1, wherein the expression cassette comprises a sequence at least about 80% identical to SEQ D NO:1.

5. The expression cassette of claim 4, wherein the expression cassette comprises a sequence at least about 90% identical to SEQ ID NO:1.

6. The expression cassette of claim 5, wherein the expression cassette comprises a sequence at least about 95% identical to SEQ ID NO:1.

7. The expression cassette of claim 6, wherein the expression cassette comprises a sequence at least about 97% identical to SEQ ID NO:1.

8. The expression cassette of claim 7, wherein the expression cassette comprises a sequence at least about 98% identical to SEQ ID NO:1.

9. The expression cassette of claim 8, wherein the expression cassette comprises a sequence at least about 99% identical to SEQ ID NO:1.

10. The expression cassette of claim 1, wherein the expression cassette comprises a nucleotide from about 1 to about 467 of SEQ ID NO:1.

11. The expression cassette of claim 1, wherein the VLIVS comprises an intron A of a hCMV IE1 gene that has a deletion between the splice acceptor and splice donor of the intron A.

12. The expression cassette of claim 1, wherein the VLIVS comprises a sequence from about $x_3$ to $x_4$ of SEQ ID NO:1, wherein $x_3$ denotes a nucleotide from about 715 to about 76 of SEQ ID NO:1 and $x_4$ denotes a nucleotide from about 1236 to about 1254 of SEQ ID NO:1.

13. The expression cassette of claim 1, further comprising an additional promoter/enhancer element or regulatory region.

14. The expression cassette of claim 13, wherein the promoter/enhancer element is an SV40 promoter/enhancer element.

15. The expression cassette of claim 13, wherein the regulatory region is an SV40 polyadenylation region.

16. The expression cassette of claim 1, further comprising a selectable marker.

17. The expression cassette of claim 16, wherein the selectable marker is selected from the group consisting of dihydrofolate reductase, GPF, neomycin, Hygro, Zeocin™, herpes simplex virus thymidine kinase, hypoxanthine-guanine phosphoribosyltransferase, adenine phosphoribosyltransferase, puromycin N-acetyl transferase or adenosine deaminase.

18. The expression cassette of claim 17, wherein the selectable marker is dihydrofolate reductase.

19. The expression cassette of claim 1, wherein the polynucleotide of interest encodes a therapeutic agent.

20. The expression cassette of claim 1, wherein the polynucleotide of interest is in the antisense orientation with respect to the promoter.

21. The expression cassette of claim 1, wherein the polynucleotide of interest is a heterologous polynucleotide.

22. The expression cassette of claim 1, wherein the polynucleotide of interest further includes transcriptional control elements.

23. The expression cassette of claim 22, wherein the transcriptional control elements are selected from the group consisting of transcriptional stop signals, polyadenylation domains and downstream enhancer elements.

24. The expression cassette of claim 1, wherein the polynucleotide of interest encodes a polypeptide of diagnostic or therapeutic use.

25. The expression cassette of claim 1, wherein the polynucleotide of interest encodes an antigenic polypeptide for use as a vaccine.

26. The expression cassette of claim 1, wherein the polyA signal domain comprises at least 100 contiguous nucleotides of SEQ ID NO:19.

27. The expression cassette of claim 1, wherein the polyA signal domain comprises SEQ ID NO:19.

28. The expression cassette of claim 1, in the form of a naked nucleic acid construct.

29. An expression vector comprising an expression cassette of claim 1.

30. A host cell comprising an expression vector of claim 29.

31. A host cell comprising an expression cassette of claim 1.

32. A method for producing a polypeptide comprising propagation of a host cell of claim 31 and expression of the polynucleotide of interest.

33. A method of delivering a therapeutic agent to an animal in need of treatment comprising propagation of a host cell of claim 31 and expression of the polynucleotide of interest.

34. A method of gene therapy to an animal in need of treatment comprising propagation of a host cell of claim 31 and expression of the polynucleotide of interest.

35. The genetic vector pV40.

36. The genetic vector pV60.

37. The genetic vector pV70.

38. The genetic vector pV80.

39. The genetic vector pV90.

40. The genetic vector pXLC.1.

41. The genetic vector pXLC.2.

42. The genetic vector pXHC.1.

43. The genetic vector pXHC.3.

44. The genetic vector pXHC.5.

* * * * *

UNITED STATES PATENT AND TRADEMARK OFFICE
CERTIFICATE OF CORRECTION

PATENT NO.        : 7,494,805 B2                                    Page 1 of 1
APPLICATION NO.   : 10/545420
DATED             : February 24, 2009
INVENTOR(S)       : Sisk et al.

It is certified that error appears in the above-identified patent and that said Letters Patent is hereby corrected as shown below:

In column 35, line 60, claim 1, please delete "seciuence" and insert therein --sequence--

In column 36, line 64, claim 4, please delete "D" and insert therein --ID--

In column 37, line 15, claim 10, please delete "467" and insert therein --1867--

In column 37, line 21, claim 12, please delete "76" and insert therein --720--

Signed and Sealed this

Fourteenth Day of April, 2009

JOHN DOLL
*Acting Director of the United States Patent and Trademark Office*

SEQUENCE LISTING

```
<160> NUMBER OF SEQ ID NOS: 21

<210> SEQ ID NO 1
<211> LENGTH: 6069
<212> TYPE: DNA
<213> ORGANISM: Homo sapiens

<400> SEQUENCE: 1
agcttgacat tgattattga ctagttatta atagtaatca attacggggt cattagttca        60
tagcccatat atggagttcc gcgttacata acttacggta aatggcccgc ctggctgacc       120
gcccaacgac ccccgcccat tgacgtcaat aatgacgtat gttcccatag taacgccaat       180
agggactttc cattgacgtc aatgggtgga gtatttacgg taaactgccc acttggcagt       240
acatcaagtg tatcatatgc caagtacgcc ccctattgac gtcaatgacg gtaaatggcc       300
cgcctggcat tatgcccagt acatgacctt atgggacttt cctacttggc agtacatcta       360
cgtattagtc atcgctatta ccatggtgat gcggttttgg cagtacatca atgggcgtgg       420
```

```
atagcggttt gactcacggg gatttccaag tctccacccc attgacgtca atgggagttt    480
gttttggcac caaaatcaac gggactttcc aaaatgtcgt aacaactccg ccccattgac    540
gcaaatgggc ggtaggcgtg tacggtggga ggtctatata agcagagctc gtttagtgaa    600
ccgtcagatc gcctggagac gccatccacg ctgttttgac ctccatagaa gacaccggga    660
ccgatccagc ctccgcggcc gggaacggtg cattggaacg cggattcccc gtgccaagag    720
tgacgtaagt accgcctata gagtctatag gcccaccccc ttggcttctt atgcatgcta    780
tactgttttt ggcttggggt ctatacaccc ccgcttcctc atgttatagg tgatggtata    840
gcttagccta taggtgtggg ttattgacca ttattgacca ctccctatt ggtgacgata    900 ctttccatta ctaatccata acatggctct ttgccacaac tctctttatt ggctatatgc    960
caatacactg tccttcagag actgacacgg actctgtatt tttacaggat ggggtctcat   1020
ttattattta caaattcaca tatacaacac caccgtcccc agtgcccgca gttttttatta  1080 aacataacgt gggatctcca cgcgaatctc gggtacgtgt tccggaacgg tggagggcag   1140
tgtagtctga gcagtactcg ttgctgccgc gcgcgccacc agacataata gctgacagac   1200
taacagactg ttccttttcca tgggtctttt ctgcagtcac cgtccttgac acgggatccg   1260
cggccgcgga tccctgcccg ggtggcatcc ctgtgacccc tccccagtgc ctctcctggt   1320
cgtggaaggt gctactccag tgcccaccag ccttgtccta ataaaattaa gttgcatcat   1380
tttgtttgac taggtgtcct tgtataatat tatggggtgg aggcgggtgg tatggagcaa   1440
ggggcaggtt gggaagacaa cctgtagggc cttcagggtc tattgggaac caggctggag   1500
tgcagtggca cgatcttggc tcgctgcaat ctccgcctcc tgggttcaag cgattctcct   1560
gcctcagtct cccgaatagt tgggattcca ggcatgcacg accaggctca gctaattttt   1620 gtattttttgg tagagacggg gtttcaccat attggccagt ctggtctcca tctcctgacc   1680
tcaggtaatc cgcccgcctc ggcctcccaa attgctggga ttacaggtat gagccactgg   1740
gcccttccct gtcctgtgat tttaaaataa ttataccagc agaaggacgt ccagacacag   1800
catgggctac ctggccatgc ccagccagtt ggacatttga gttgtttgct tggcactgtc   1860
ctctcatgaa ttcgtcgaca gatctgcgca gcaccatggc ctgaaataac ctctgaaaga   1920
ggaacttggt taggtacctt ctgaggcgga aagaaccagc tgtggaatgt gtgtcagtta   1980
gggtgtggaa agtccccagg ctccccagca ggcagaagta tgcaaagcat gcatctcaat   2040
tagtcagcaa ccaggtgtgg aaagtcccca ggctccccag caggcagaag tatgcaaagc   2100
atgcatctca attagtcagc aaccatagtc ccgcccctaa ctccgcccat cccgccccta   2160
actccgccca gttccgccca ttctccgccc catggctgac taatttttttt tatttatgca   2220 gaggccgagg ccgcctcggc ctctgagcta ttccagaagt agtgaggagg cttttttgga   2280
ggcctaggct tttgcaaaaa gcttgattct tctgacacaa cagtctcgaa cttaagctgc   2340
agaagttggt cgtgaggcac tgggcaggta agtatcaagg ttacaagaca ggtttaagga   2400
gaccaataga aactgggctt gtcgagacag agaagactct tgcgtttctg ataggcacct   2460
attggtctta ctgacatcca ctttgccttt ctctccacag gtgtccactc ccagttcaat   2520
tacagctctt aaggctagag tacttaatac gactcactat aggctagcat ggttcgacca   2580
ttgaactgca tcgtcgccgt gtcccaaaat atggggattg gcaagaacgg agacctaccc   2640
tggcctccgc tcaggaacga gttcaagtac ttccaaagaa tgaccacaac ctcttcagtg   2700
gaaggtaaac agaatctggt gattatgggt aggaaaacct ggttctccat tcctgagaag   2760
aatcgacctt taaaggacag aattaatata gttctcagta gagaactcaa agaaccacca   2820
```

```
cgaggagctc attttcttgc caaaagtttg gatgatgcct taagacttat tgaacaaccg    2880
gaattggcaa gtaaagtaga catggtttgg atagtcggag gcagttctgt ttaccaggaa    2940
gccatgaatc aaccaggcca cctcagactc tttgtgacaa ggatcatgca ggaatttgaa    3000
agtgacacgt ttttcccaga aattgatttg gggaaatata aacttctccc agaataccca    3060
ggcgtcctct ctgaggtcca ggaggaaaaa ggcatcaagt ataagtttga agtctacgag    3120
aagaaagact aactcgagaa ttcacgcgtg gtacctctag agtcgacccg ggcggccggc    3180
cgcttcgagc agacatgata agatacattg atgagtttgg acaaaccaca actagaatgc    3240
agtgaaaaaa atgctttatt tgtgaaattt gtgatgctat tgctttattt gtaaccatta    3300
taagctgcaa taaacaagtt aacaacaaca attgcattca ttttatgttt caggttcagg    3360
gggaggtgtg ggaggttttt taaagcaagt aaaacctcta caaatgtggt aaaatcgata    3420
aggatctgtc gacgaattca ctggccgtcg ttttacaacg tcgtgactgg gaaaaccctg    3480
gcgttaccca acttaatcgc cttgcagcac atccccettt cgccagctgg cgtaatagcg    3540
aagaggcccg caccgatcgc ccttcccaac agttgcgcag cctgaatggc gaatggcgcc    3600
tgatgcggta ttttctcctt acgcatctgt gcggtatttc acaccgcata tggtgcactc    3660
tcagtacaat ctgctctgat gccgcatagt taagccagcc ccgacacccg ccaacacccg    3720
ctgacgcgcc ctgacgggct tgtctgctcc cggcatccgc ttacagacaa gctgtgaccg    3780
tctccgggag ctgcatgtgt cagaggtttt caccgtcatc accgaaacgc gcgagacgaa    3840
agggcctcgt gatacgccta ttttataggt taatgtcat gataataatg gtttcttaga    3900
cgtcaggtgg cacttttcgg ggaaatgtgc gcggaacccc tatttgttta ttttctaaa    3960 tacattcaaa tatgtatccg ctcatgagac aataaccctg ataaatgctt caataatatt    4020
gaaaaaggaa gagtatgagt attcaacatt tccgtgtcgc ccttattccc ttttttgcgg    4080
cattttgcct tcctgttttt gctcacccag aaacgctggt gaaagtaaaa gatgctgaag    4140
atcagttggg tgcacgagtg ggttacatcg aactggatct caacagcggt aagatccttg    4200
agagttttcg ccccgaagaa cgttttccaa tgatgagcac ttttaaagtt ctgctatgtg    4260
gcgcggtatt atcccgtatt gacgccgggc aagagcaact cggtcgccgc atacactatt    4320
ctcagaatga cttggttgag tactcaccag tcacagaaaa gcatcttacg gatggcatga    4380
cagtaagaga attatgcagt gctgccataa ccatgagtga taacactgcg gccaacttac    4440
ttctgacaac gatcggagga ccgaaggagc taaccgcttt tttgcacaac atggggatc    4500 atgtaactcg ccttgatcgt tgggaaccgg agctgaatga agccatacca aacgacgagc    4560
gtgacaccac gatgcctgta gcaatggcaa caacgttgcg caaactatta actggcgaac    4620
tacttactct agcttcccgg caacaattaa tagactggat ggaggcggat aaagttgcag    4680
gaccacttct gcgctcggcc cttccggctg gctggtttat tgctgataaa tctggagccg    4740
gtgagcgtgg gtctcgcggt atcattgcag cactggggcc agatggtaag ccctcccgta    4800
tcgtagttat ctacacgacg gggagtcagg caactatgga tgaacgaaat agacagatcg    4860
ctgagatagg tgcctcactg attaagcatt ggtaactgtc agaccaagtt tactcatata    4920
tactttagat tgatttaaaa cttcattttt aatttaaaag gatctaggtg aagatccttt    4980
ttgataatct catgaccaaa atcccttaac gtgagttttc gttccactga gcgtcagacc    5040
ccgtagaaaa gatcaaagga tcttcttgag atccttttt tctgcgcgta atctgctgct    5100
tgcaaacaaa aaaaccaccg ctaccagcgg tggtttgttt gccggatcaa gagctaccaa    5160
```

-continued

| | |
|---|---|
| ctctttttcc gaaggtaact ggcttcagca gagcgcagat accaaatact gtccttctag | 5220 |
| tgtagccgta gttaggccac cacttcaaga actctgtagc accgcctaca tacctcgctc | 5280 |
| tgctaatcct gttaccagtg gctgctgcca gtggcgataa gtcgtgtctt accgggttgg | 5340 |
| actcaagacg atagttaccg gataaggcgc agcggtcggg ctgaacgggg ggttcgtgca | 5400 |
| cacagcccag cttggagcga acgacctaca ccgaactgag atacctacag cgtgagctat | 5460 |
| gagaaagcgc cacgcttccc gaagggagaa aggcggacag gtatccggta agcggcaggg | 5520 |
| tcggaacagg agagcgcacg agggagcttc caggggaaa cgcctggtat ctttatagtc | 5580 |
| ctgtcgggtt tcgccacctc tgacttgagc gtcgatttt tgtgatgctcg tcagggggc | 5640 |
| ggagcctatg gaaaaacgcc agcaacgcgg cctttttacg gttcctggcc ttttgctggc | 5700 |
| cttttgctca catgttcttt cctgcgttat cccctgattc tgtggataac cgtattaccg | 5760 |
| cctttgagtg agctgatacc gctcgccgca gccgaacgac cgagcgcagc gagtcagtga | 5820 |
| gcgaggaagc ggaagagcgc ccaatacgca aaccgcctct ccccgcgcgt tggccgattc | 5880 |
| attaatgcag ctggcacgac aggtttcccg actggaaagc gggcagtgag cgcaacgcaa | 5940 |
| ttaatgtgag ttagctcact cattaggcac cccaggcttt acactttatg cttccggctc | 6000 |
| gtatgttgtg tggaattgtg agcggataac aatttcacac aggaaacagc tatgaccatg | 6060 |
| attacgcca | 6069 |

```
<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
```

| | |
|---|---|
| tttaagcttg acattgatta ttgactag | 28 |

```
<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
```

| | |
|---|---|
| ttttggatcc ctgtcaagga cggtgactgc | 30 |

```
<210> SEQ ID NO 4
<211> LENGTH: 15
<212> TYPE: DNA
<213> ORGANISM: Artificial Sequence
<220> FEATURE:
<223> OTHER INFORMATION: adaptor oligonucleotide

<400> SEQUENCE: 4
```

| | |
|---|---|
| gatcgatgaa ttcgg | 15 |

```
<210> SEQ ID NO 5
<211> LENGTH: 13
<212> TYPE: DNA
<213> ORGANISM: Artificial Sequence
<220> FEATURE:
<223> OTHER INFORMATION: adaptor oligonucleotide

<400> SEQUENCE: 5
```

| | |
|---|---|
| ctacttaagc cgc | 13 |

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
ttttggatcc atgtactggg tgaagcag                                    28

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
gcccggatcc tcatttaccc ggagacag                                    28

<210> SEQ ID NO 8
<211> LENGTH: 53
<212> TYPE: DNA
<213> ORGANISM: Artificial Sequence
<220> FEATURE:
<223> OTHER INFORMATION: primer

<400> SEQUENCE: 8
ttttctgcag tcaccgtcct tgacacggga tccatggact ggaccttgga ggg        53

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
ctgaggagac ggtgaccagg gtcccttggc ccc                              33

<210> SEQ ID NO 10
<211> LENGTH: 12
<212> TYPE: DNA
<213> ORGANISM: Artificial Sequence
<220> FEATURE:
<223> OTHER INFORMATION: adaptor oligonucleotide

<400> SEQUENCE: 10
aattcgtcga ca                                                     12

<210> SEQ ID NO 11
<211> LENGTH: 12
<212> TYPE: DNA
<213> ORGANISM: Artificial Sequence
<220> FEATURE:
<223> OTHER INFORMATION: adaptor oligonucleotide

<400> SEQUENCE: 11
gcagctgtct ag                                                     12

<210> SEQ ID NO 12
<211> LENGTH: 14
<212> TYPE: DNA
<213> ORGANISM: Artificial Sequence
<220> FEATURE:

```
<223> OTHER INFORMATION: synthetically generated oligonucleotide

<400> SEQUENCE: 12
gatccgcggc cgcg                                                            14

<210> SEQ ID NO 13
<211> LENGTH: 13
<212> TYPE: DNA
<213> ORGANISM: Artificial Sequence
<220> FEATURE:
<223> OTHER INFORMATION: synthetically generated oligonucleotide

<400> SEQUENCE: 13
gatccgcggc cgc                                                             13

<210> SEQ ID NO 14
<211> LENGTH: 14
<212> TYPE: DNA
<213> ORGANISM: Artificial Sequence
<220> FEATURE:
<223> OTHER INFORMATION: synthetically generated oligonucleotide

<400> SEQUENCE: 14
cgccggcgcc tagg                                                            14

<210> SEQ ID NO 15
<211> LENGTH: 16
<212> TYPE: DNA
<213> ORGANISM: Artificial Sequence
<220> FEATURE:
<223> OTHER INFORMATION: synthetically generated oligonucleotide

<400> SEQUENCE: 15
ggatccctgc ccgggt                                                          16

<210> SEQ ID NO 16
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 16
ggatccgcgg ccgcggatcc ctgcccgggt                                           30

<210> SEQ ID NO 17
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 17
ggatccgcgg ccgccatg                                                        18

<210> SEQ ID NO 18
<211> LENGTH: 2660
<212> TYPE: DNA
<213> ORGANISM: Homo sapiens

<400> SEQUENCE: 18
gaattcagca ctgaatcatg cccagaaccc ccgcaatcta ttggctgtgc tttggcccct          60
tttcccaaca cacacattct gtctggtggg tggaggggaa acatgcgggg aggaggaaag         120
gaataggata gagagtggga tggggtcggt aggggtctca aggactggcc tatcctgaca         180
```

-continued

```
tccttctccg cgttcaggtt ggccaccatg gcctgctgcc agagggcacc cacgtgaccc        240
ttaaagagag acaagttgg gtggtatctc tggctgacat tctgtgcaca accctcacaa         300
cgctggtgat ggtgggaagg gaaagatgac aagtcagggg gcatgatccc agcatgtgtg        360
ggaggagctt ctaaattatc cattagcaca agcccgtcag tggccccagg cctaaacatg        420
cagagaaaca ggtgaggaga agcagcgaga gagaaggggc caggtataaa aagggcccac        480
aagagaccag ctcaaggatc ccaaggccca actccccgaa ccactcaggg tcctgtggac        540
agctcactag cggcaatggc tgcaggtaag cgcccctaaa atcccttttgg cacaatgtgt       600 cctgaggga gaggcggcgt cctgtagatg ggacggggc actaaccctc aggtttgggg         660
cttatgaatt ttagctatcg ccatctaagc ccagtatttg gccaatctct gaatgttcct        720
ggtccctgga ggaggcagag agagagagag agaaaaaaaa acccagctc ctggaacagg         780 gagagcgctg gcctcttgct ctccagctcc ctctgttgcc tccggttttct ccccaggctc       840 ccggacgtcc ctgctcctgg cttttggcct gctctgcctg cctggcttc aagagggcag        900 tgccttccca accattccct tatccaggct ttttgacaac gctatgctcc cgcccgtcg        960 cctgtaccag ctggcatatg acacctatca ggagtttgta agctcttggg taatgggtgc       1020
gcttcagagg tggcaggaag gggtgaattt ccccgctgg gaagtaatgg gaggagacta        1080
aggagctcag ggttgttttc tgaagtgaaa atgcaggcag atgagcatac gctgagtgag       1140
gttcccagaa aagtaacaat gggagcaggt ctccagcata accttggtg ggcggtcctt        1200 ctcctaggaa gaagcctata tcctgaagga gcagaagtat tcattcctgc agaacccca        1260 gacctccctc tgcttctcag agtctattcc aacaccttcc aacagggtga aaacgcagca      1320
gaaatctgtg agtggatgcc ttctccccag gtgggatggg gtagacctgt ggtcagagcc      1380
cccgggcagc acagccactg ccggtccttc ccctgcagaa cctagagctg ctccgcatct      1440
ccctgctgct catccagtca tggctggagc ccgtgcagct cctcaggagc gtcttcgcca      1500
acagcctggt gtatggcgcc tcggacagca acgtctatcg ccacctgaag gacctagagg      1560
aaggcatcca aacgctgatg tgggtgaggg tggcaccagg atccaatcct ggggccccac      1620
tggcttccag ggactgggga gagaaacact gctgccctct ttttagcagt caggcgctga      1680
cccaagagaa ctcaccgtat tcttcatttc ccctcgtgaa tcctccaggc ctttctctac      1740
aacctggagg ggagggagga aaatggatga atgagagagg gagggaacag tgcccaagcg      1800
cttggcctct ccttctcttc cttcactttg cagaggctgg aagatggcag cccccggact      1860
gggcagatct tcaatcagtc ctacagcaag tttgacacaa aatcgcacaa cgatgacgca      1920
ctgctcaaga actacgggct gctctactgc ttcaggaagg acatggacaa ggtcgagaca      1980
ttcctgcgca tcgtgcagtg ccgctctgtg gagggcagct gtggcttcta gctgcccggg     2040
tggcatccct gtgaccctc cccagtgcct ctcctggtcg tggaaggtgc tactccagtg      2100
cccaccagcc ttgtcctaat aaaattaagt tgcatcattt tgtttgacta ggtgtccttg     2160
tataatatta tggggtggag gcgggtggta tggagcaagg ggccaggttg ggaagacaac     2220
ctgtagggcc ttcagggtct attcgggaac caggctggag tgcagtggca gtcttggctc      2280
gctgcaatct ccgcctcctg ggttcaagcg attctcctgc ctcagtctcc cgaatagttg      2340
cgattccagg catgcaagac caggctcagc taatttttgt atttttggta gagacggggt     2400
ttcaccatat tggccagtct ggtctccatc tcctgacctc aggtaatccg cccgcctcgg     2460
cctcccaaat tgctgggatt acaggtatga gccactgggc ccttccctgt cctgtgattt      2520
```

```
taaaataatt ataccagcag aaggacgtcc agacacagca tgggctacct ggccatgccc    2580
agccagttgg acatttgagt tgtttgcttg gcactgtcct ctcatgcatt gggtccactc    2640
agtagatgct tgttgaattc                                                 2660

<210> SEQ ID NO 19
<211> LENGTH: 594
<212> TYPE: DNA
<213> ORGANISM: Homo sapiens

<400> SEQUENCE: 19
ctgcccgggt ggcatccctg tgaccgctcc ccagtgcctc tcctggtcgt ggaaggtgct      60
actccagtgc ccaccagcct tgtcctaata aaattaagtt gcatcatttt gtttgactag     120
gtgtccttgt ataatattat ggggtggagg cgggtggtat ggagcaaggg gccaggttgg     180
gaagacaacc tgtagggcct tcagggtcta ttcgggaacc aggctggagt gcagtggcag     240
tcttggctcg ctgcaatctc cgcctcctgg gttcaagcga ttctcctgcc tcagtctccc     300
gaatagttgc gattccaggc atgcaagacc aggctcagct aattttgta ttttggtag      360 agacggggtt tcaccatatt ggccagtctg gtctccatct cctgacctca ggtaatccgc     420
ccgcctcggc ctcccaaatt gctgggatta caggtatgag ccactgggcc cttccctgtc     480
ctgtgatttt aaaataatta taccagcaga aggacgtcca gacacagcat gggctacctg     540
gccatgccca gccagttgga catttgagtt gtttgcttgg cactgtcctc tcat            594

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
ttttggatcc ctgcccgggt ggcatcc                                          27

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
ttttgaattc atgagaggac agtgccaagc                                       30
```